US012319121B2

(12) United States Patent
Matsui et al.

(10) Patent No.: US 12,319,121 B2
(45) Date of Patent: Jun. 3, 2025

(54) QUALITY DETERMINATION DEVICE

(71) Applicant: DAIKIN INDUSTRIES, LTD., Osaka (JP)

(72) Inventors: Hidenori Matsui, Osaka (JP); Naohiro Tanaka, Osaka (JP); Shouichi Tanno, Osaka (JP); Masataka Nakano, Osaka (JP); Motomi Nishimoto, Osaka (JP); Kiichirou Satou, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 302 days.

(21) Appl. No.: 17/686,815

(22) Filed: Mar. 4, 2022

(65) Prior Publication Data

US 2022/0185064 A1 Jun. 16, 2022

Related U.S. Application Data

(63) Continuation of application No. PCT/JP2020/036632, filed on Sep. 28, 2020.

(30) Foreign Application Priority Data

Sep. 30, 2019 (JP) .................................. 2019-179867

(51) Int. Cl.
*B60H 1/00* (2006.01)
*G01N 21/64* (2006.01)
(Continued)

(52) U.S. Cl.
CPC ....... *B60H 1/00742* (2013.01); *B60H 1/0073* (2019.05); *B60H 1/00978* (2013.01);
(Continued)

(58) Field of Classification Search
CPC .. G01N 21/6486; G01N 33/025; G05B 17/02; B60H 1/008
See application file for complete search history.

(56) References Cited

U.S. PATENT DOCUMENTS

| 5,621,162 A * | 4/1997 | Yun ...................... G01N 27/125 |
| | | 73/31.06 |
| 2002/0011567 A1* | 1/2002 | Ozanich ................ G01J 3/0224 |
| | | 250/326 |

(Continued)

FOREIGN PATENT DOCUMENTS

| CN | 106472659 A * | 3/2017 | ........... A23B 7/0408 |
| CN | 108507272 A | 9/2018 | |

(Continued)

OTHER PUBLICATIONS

JP-2018096712-A Translation (Year: 2018).*

(Continued)

*Primary Examiner* — Schyler S Sanks
(74) *Attorney, Agent, or Firm* — Birch, Stewart, Kolasch & Birch, LLP

(57) ABSTRACT

A quality determination apparatus includes a state detector and a main processing unit. The state detector detects a state index. The state index is an index indicating a state of a target article contained in a storage space where an internal environment is controlled. The main processing unit performs a determination operation. The determination operation is an operation of determining whether a sign condition indicating a sign of degradation of the target article is met based on the state index detected by the state detector.

10 Claims, 13 Drawing Sheets

(51) Int. Cl.
    *G01N 33/02* (2006.01)
    *G05B 15/02* (2006.01)
(52) U.S. Cl.
    CPC ....... *G01N 21/6486* (2013.01); *G01N 33/025* (2013.01); *G05B 15/02* (2013.01)

(56) References Cited

U.S. PATENT DOCUMENTS

| | | |
|---|---|---|
| 2003/0146394 A1 | 8/2003 | Prange et al. |
| 2006/0064313 A1* | 3/2006 | Steinbarth .......... G06Q 10/1057 705/322 |
| 2017/0156594 A1 | 6/2017 | Stivoric et al. |
| 2017/0184333 A1 | 6/2017 | Lukasse |
| 2018/0224150 A1 | 8/2018 | Lewis et al. |
| 2019/0141903 A1 | 5/2019 | Takayama et al. |
| 2019/0236536 A1 | 8/2019 | Poolman et al. |
| 2019/0285603 A1* | 9/2019 | Velez .................... G06Q 10/04 |
| 2020/0112038 A1* | 4/2020 | Ryu ................. H01M 8/04037 |
| 2020/0126233 A1 | 4/2020 | Shinoda et al. |
| 2020/0293984 A1 | 9/2020 | Beasley et al. |
| 2020/0298672 A1 | 9/2020 | Yasar et al. |
| 2021/0161075 A1 | 6/2021 | Takayama et al. |

FOREIGN PATENT DOCUMENTS

| | | | |
|---|---|---|---|
| CN | 109073316 A | 12/2018 | |
| CN | 109154470 A | 1/2019 | |
| JP | 7-83557 A | 3/1995 | |
| JP | 7-92121 A | 4/1995 | |
| JP | 2001-41640 A | 2/2001 | |
| JP | 2006-300351 A | 11/2006 | |
| JP | 2015-65965 A | 4/2015 | |
| JP | 2018-133296 A | 7/2016 | |
| JP | 2017-15291 A | 1/2017 | |
| JP | 2017-89913 A | 5/2017 | |
| JP | 2017-122569 A | 7/2017 | |
| JP | 2017-190935 A | 10/2017 | |
| JP | 2018-29568 A | 3/2018 | |
| JP | 2018-96712 A | 6/2018 | |
| JP | 2018096712 A * | 6/2018 | |
| JP | 2019-16305 A | 1/2019 | |
| WO | WO-2017172701 A1 * | 10/2017 | ......... B60H 1/00657 |

OTHER PUBLICATIONS

WO-2017172701-A1 Translation (Year: 2017).*
CN-106472659-A Translation (Year: 2017).*
Nedbal, Ladislav, et al. "Postharvest imaging of chlorophyll fluorescence from lemons can be used to predict fruit quality." Photosynthetica 38 (2000): 571-579. (Year: 2000).*
Japanese Notice of Reasons for Revocation dated Sep. 8, 2023 for Application No. 2021-551252 with an English translation.
Extended European Search Report for European Application No. 20871148.1, dated Aug. 22, 2023.
Japanese Notice of Opposition for Japanese Application No. 2023-700560, dated Jun. 29, 2023, with an English translation.
Murata, "Optimum Temperature for Storage of Fruit and Vegetables with Reference to Chilling Injury", Paper of Japan Society of Refrigerating and Air Conditioning Engineers, vol. 3, No. 1, 1986, pp. 1-11, with an English abstract.
Nagata, "After-harvesting Physiology Regarding Freshness of Fruits and Vegetables", Shokuryo, Food Science and Technology, vol. 56, Mar. 29, 2018, pp. 43-66, (31 pages total), with a partial English translation.
International Search Report issued in PCT/JP2020/036632, dated Dec. 1, 2020.
Kawabata et al., "Measurement of Preciseness in Daily Actions to Detect Decline of Living Willingness," FIT, 2013, total 3 pages.
English translation of the International Preliminary Report on Patentability and Written Opinion of the International Searching Authority for International Application No. PCT/JP2020/036632, dated Apr. 14, 2022.

* cited by examiner

QUALITY DETERMINATION DEVICE

CROSS REFERENCE TO RELATED APPLICATIONS

This application is a Continuation of PCT International Application No. PCT/JP2020/036632, filed on Sep. 28, 2020, which claims priority under 35 U.S.C. 119(a) to Patent Application No. 2019-179867, filed in Japan on Sep. 30, 2019, all of which are hereby expressly incorporated by reference into the present application.

TECHNICAL FIELD

The present disclosure relates to a quality determination apparatus.

BACKGROUND ART

For maintenance of the quality of a target article contained in a storage space, an internal environment of the storage space (specifically, for example, the temperature and composition of the air in the storage space) is controlled. For example. Patent Document 1 discloses a refrigeration apparatus directed to a container used for marine transportation. The refrigeration apparatus controls the temperature and composition (specifically, for example, oxygen concentration and carbon dioxide concentration) of the air in the container. Such an apparatus for controlling the internal environment of the storage space adjusts the temperature and composition of the air in the storage space so that the temperature and composition of the air in the storage space reach values previously set by an operator.

CITATION LIST

Patent Document

Patent Document 1: Japanese Unexamined Patent Publication No. 2017-190935

SUMMARY

A first aspect of the present disclosure is directed to a quality determination apparatus (13), including: a state acquisition unit (75, 101) configured to acquire a state index indicating a state of a target article (7) contained in a storage space (5) where an internal environment is controlled from a state detector (15) that detects the state index; and a main processing unit (64) configured to perform a determination operation of determining whether a sign condition indicating a sign of degradation of the target article (7) is met based on the state index acquired by the state acquisition unit (75, 101).

DESCRIPTION OF EMBODIMENTS

First Embodiment

A first embodiment will be described below. A quality determination apparatus (13) of the present embodiment is provided for an internal environment control system (10).

Figure 1:
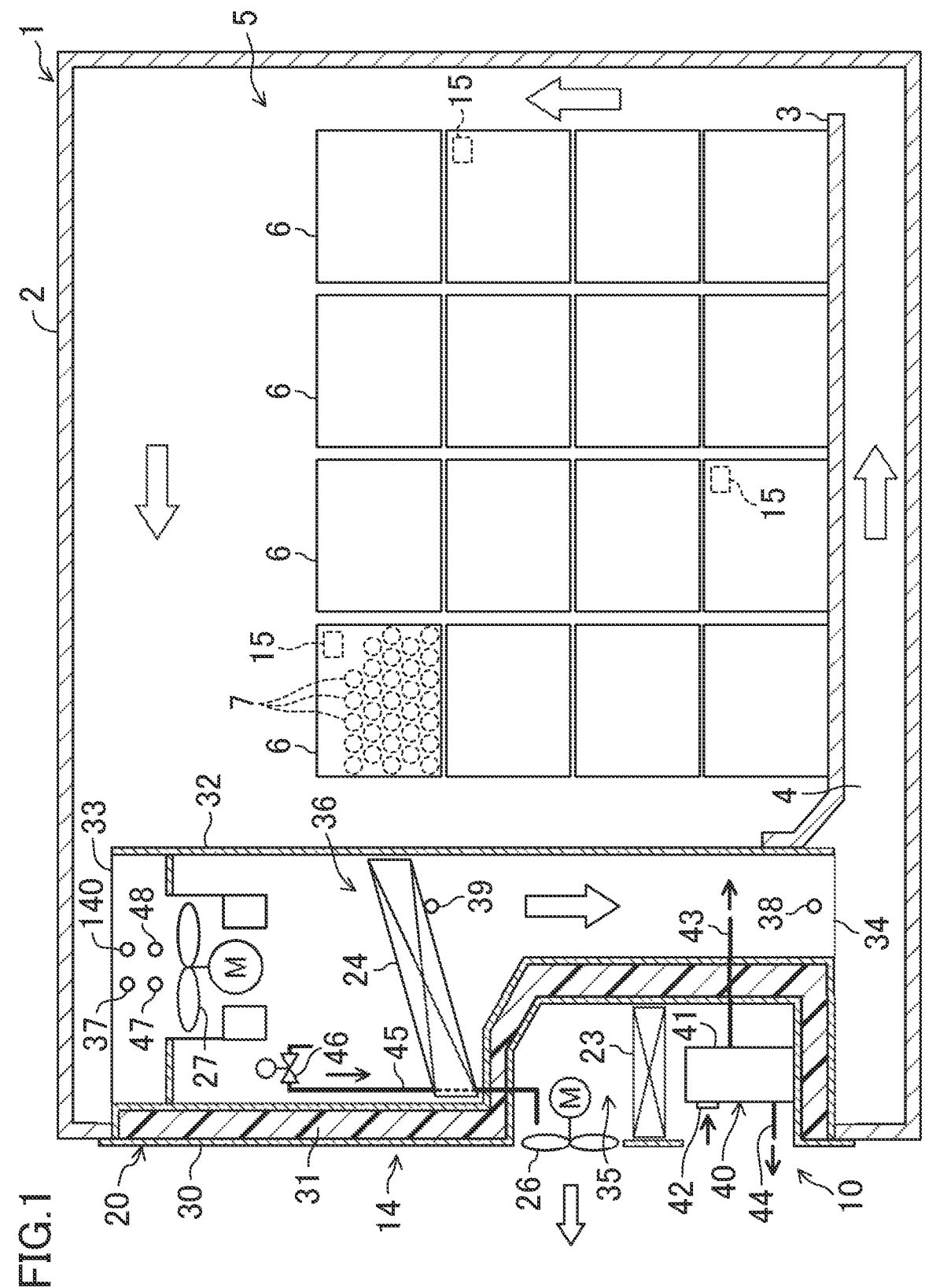
FIG. 1 is a schematic cross-sectional view of a container refrigeration apparatus of an internal environment control system and a shipping container equipped with the container refrigeration apparatus.

As illustrated in FIG. 1, the internal environment control system (10) is provided for a shipping container (1) used for so-called CA (controlled atmosphere) transport. The shipping container (1) provided with the internal environment control system (10) is used to transport target articles (7). The target articles (7) contained in the shipping container (1) are fresh produce, such as fruits and vegetables.

Figure 4:
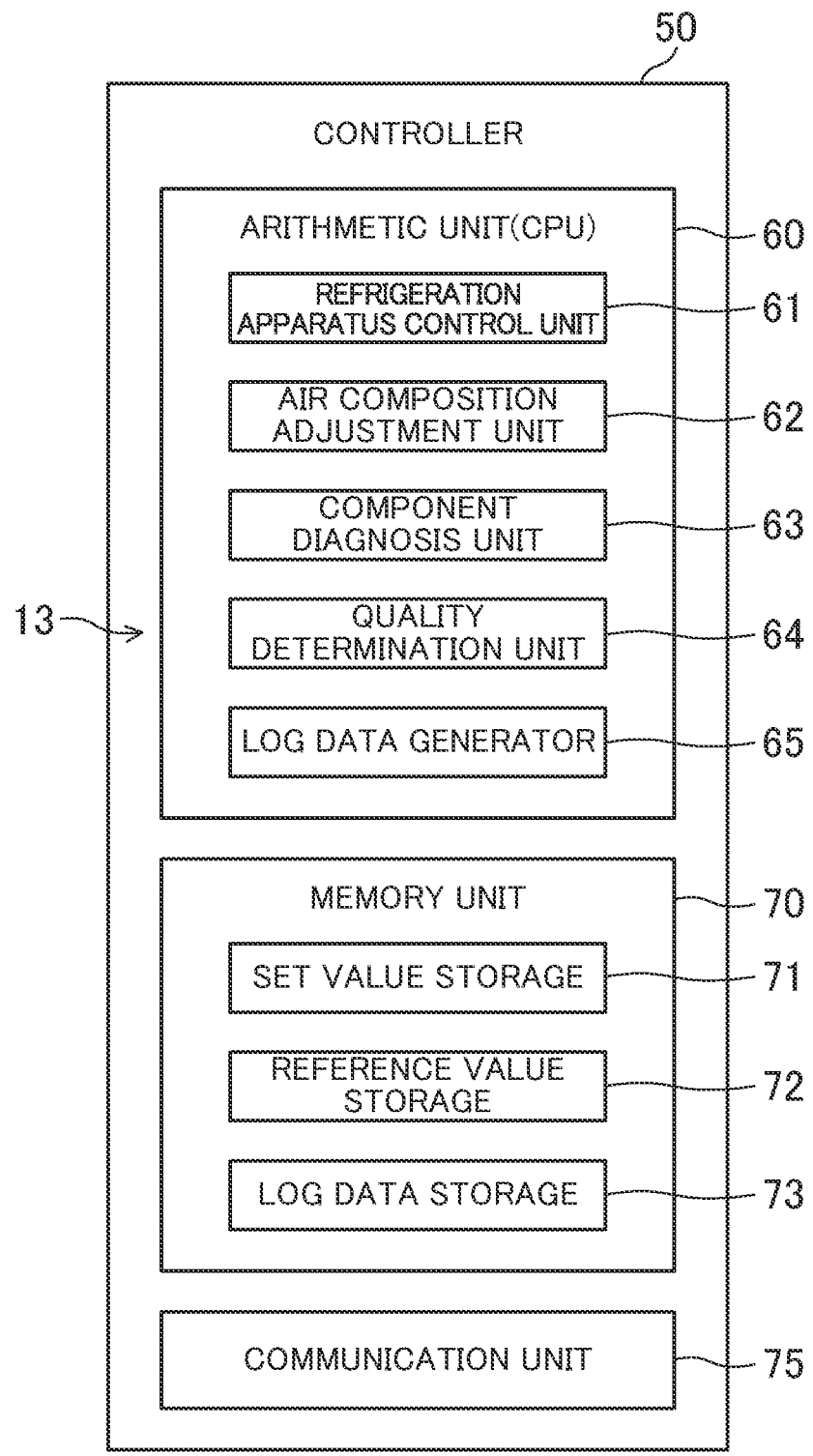
FIG. 4 is a block diagram illustrating a configuration of a controller of the internal environment control system.

As illustrated in FIGS. 1 and 4, the internal environment control system (10) includes a container refrigeration apparatus (20), an air composition adjustment apparatus (40), an operation panel (80), state index sensors (15), and a controller (50).

The controller (50) and the state index sensors (15) constitute the quality determination apparatus (13) of the present embodiment. The quality determination apparatus

(13) determines whether there is a sign of degradation of the target articles (7) contained in the shipping container (1).

The container refrigeration apparatus (20), the air composition adjustment apparatus (40), and the controller (50) constitute an environment adjustment apparatus (14). The environment adjustment apparatus (14) controls the internal environment of the shipping container (I) so that the internal environment becomes a set environment. That is, the environment adjustment apparatus (14) controls the internal environment of the shipping container (1) so that environmental indexes reach respective set values. The environmental indexes are physical quantities indicating the internal environment of the shipping container (1), e.g., the temperature, humidity, oxygen concentration, and carbon dioxide concentration of the air in the container.

The shipping container (1) used as a warehouse has a container body (2) in the shape of an elongated rectangular parallelepiped box. One end face of the container body (2) is open. The container refrigeration apparatus (20) is attached to block the open end of the container body (2). Space inside the container body (2) constitutes a cargo space (5) for storing cargos (6). The cargo space (5) is a storage space. The cargos (6) are boxes of the target articles (7).

A floorboard (3) on which the cargos (6) are to be placed is disposed at the bottom of the cargo space (5). An underfloor path (4) through which air blown from the container refrigeration apparatus (20) passes is formed between the floorboard (3) and a bottom plate of the container body (2). The underfloor path (4) extends along the bottom plate of the container body (2) in the longitudinal direction of the container body (2). One end of the underfloor path (4) is connected to an outlet (34) of the container refrigeration apparatus (20), and the other end communicates with a space above the floorboard (3) (i.e., the space for storing the cargos (6)).

—Container Refrigeration Apparatus—

As illustrated in FIG. 1, the container refrigeration apparatus (20) includes a casing (30), a refrigerant circuit (21) that performs a refrigeration cycle, an external fan (26), an internal fan (27), and an operation panel (80).

<Casing>

The casing (30) includes a casing body (31) and a backboard (32). The casing (30) is provided with the refrigerant circuit (11), the external fan (26), and the internal fan (27).

The casing body (31) has a lower portion recessed toward the cargo space (5) of the shipping container (1). The lower portion of the casing body (31) forms an external equipment room (35) communicating with a space outside the shipping container (1). The external fan (26) is disposed in the external equipment room (35).

The backboard (32) is a substantially rectangular flat plate-shaped member. The backboard (32) is disposed closer to the cargo space (5) of the shipping container (1) than the casing body (31), and forms an inside air flow path (36) between the backboard (32) and the casing body (31).

The inside air flow path (36) has an upper end serving as an inlet (33) of the casing (30), and a lower end as an outlet (34) of the casing (30). The inside air flow path (36) communicates with the cargo space (5) via the inlet (33), and with the underfloor path (4) via the outlet (34). The internal fan (27) is disposed above the inside air flow path (36).

<Refrigerant Circuit>

Figure 2:
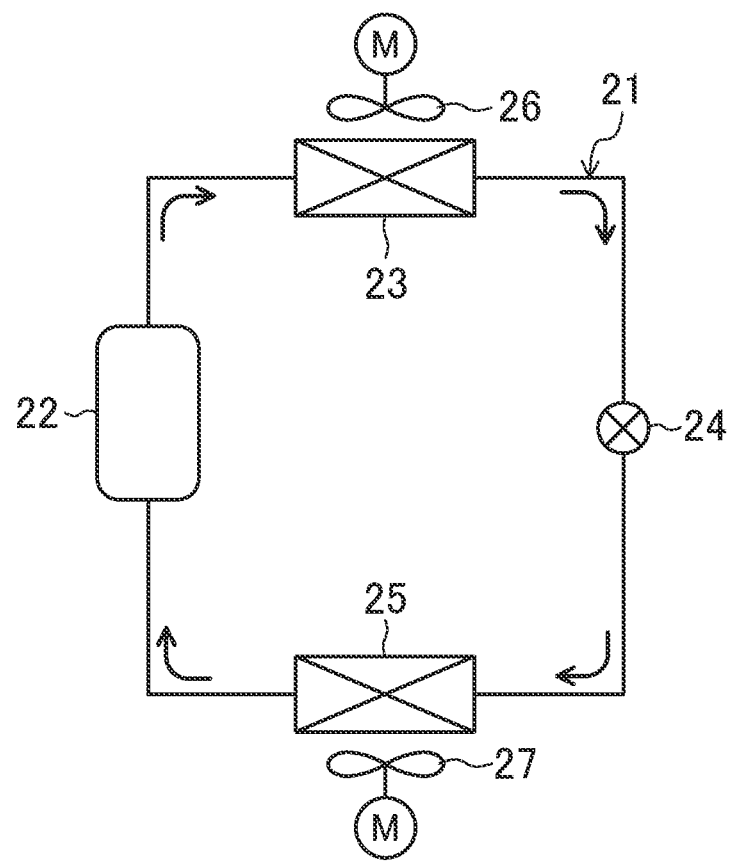
FIG. 2 is a piping system diagram of a refrigerant circuit included in the container refrigeration apparatus.

As illustrated in FIG. 2, the refrigerant circuit (21) is a closed circuit in which a compressor (22), a condenser (23), an expansion valve (24), and an evaporator (25) are connected together in this order by piping. When the compressor (22) is actuated, a refrigerant circulates through the refrigerant circuit (21) to perform a vapor compression refrigeration cycle.

As illustrated in FIG. 1, the condenser (23) is disposed on the suction side of the external fan (26) in the external equipment room (35), and the evaporator (25) is disposed in the inside air flow path (36) below the internal fan (27). Although not shown in FIG. 1, the compressor (22) is disposed in the external equipment room (35).

<Sensors>

The container refrigeration apparatus (20) includes a suction temperature sensor (37), a blowout temperature sensor (38), and an evaporator temperature sensor (39).

The suction temperature sensor (37) is disposed upstream of the evaporator (25) in the inside air flow path (36). The suction temperature sensor (37) measures the temperature of the inside air sucked into the inside air flow path (36) from the cargo space (5) through the inlet (33). The temperature of the inside air measured by the suction temperature sensor (37) is an environmental index which is a physical quantity indicating the internal environment.

The blowout temperature sensor (38) is disposed downstream of the evaporator (25) in the inside air flow path (36). The blowout temperature sensor (38) measures the temperature of the air blown from the outlet (34) to the underfloor path (4).

The evaporator temperature sensor (39) is attached to the evaporator (25). The evaporator temperature sensor (39) measures the temperature of the surface of the evaporator (25).

—Air Composition Adjustment Apparatus—

The air composition adjustment apparatus (40) is an apparatus for adjusting the composition of the air in the cargo space (5) of the shipping container (1). As illustrated in FIG. 1, the air composition adjustment apparatus (40) includes a main unit (41) and a ventilation exhaust pipe (45). The main unit (41) is disposed in the external equipment room (35) of the container refrigeration apparatus (20).

<Main Unit>

Although not shown, the main unit (41) of the air composition adjustment apparatus (40) contains two adsorption columns, a pressurizing pump that supplies pressurized air to the adsorption columns, and a depressurizing pump that sucks the air from the adsorption columns. The air composition adjustment apparatus (40) modifies the air outside the container (i.e., atmospheric air) to generate modified air having a composition different from that of the outside air by a so-called pressure swing adsorption (PSA) method. The modified air has a higher nitrogen concentration and a lower oxygen concentration than the outside air.

The main unit (41) includes an outside air inlet (42) through which the outside air is taken into the main unit (41). A supply pipe (43) and an oxygen discharge pipe (44) are connected to the main unit (41). The supply pipe (43) is a pipe for introducing the modified air (low oxygen concentration air) generated in the main unit (41) into the cargo space (5), and has a terminal end open to the inside air flow path (36). The oxygen discharge pipe (44) is a pipe for discharging high oxygen concentration air generated in the main unit (41) to the outside of the container, and has a terminal end open to the external equipment room (35).

<Ventilation Exhaust Pipe>

The ventilation exhaust pipe (45) is a pipe for discharging the air in the shipping container (1) to the outside. The ventilation exhaust pipe (45) has one end open to the inside air flow path (36) and the other end open to the external equipment room (35). The ventilation exhaust pipe (45) is provided with a ventilation exhaust valve (46). The ventilation exhaust valve (46) is an on-off valve made of an electromagnetic valve.

<Sensors>

The air composition adjustment apparatus (40) includes an oxygen concentration sensor (47), a carbon dioxide concentration sensor (48), and an ethylene concentration sensor (140).

The oxygen concentration sensor (47) and the carbon dioxide concentration sensor (48) are disposed upstream of the evaporator (25) in the inside air flow path (36). The oxygen concentration sensor (47) measures the oxygen concentration of the inside air sucked into the inside air flow path (36) through the inlet (33). The carbon dioxide concentration sensor (48) measures the carbon dioxide concentration of the inside air sucked into the inside air flow path (36) through the inlet (33). The ethylene concentration sensor (140) measures the ethylene concentration of the inside air sucked into the inside air flow path (36) through the inlet (33).

The oxygen concentration of the inside air measured by the oxygen concentration sensor (47), the carbon dioxide concentration of the inside air measured by the carbon dioxide concentration sensor (48), and the ethylene concentration of the inside air measured by the ethylene concentration sensor (140) are environmental indexes that are physical quantities indicating the internal environment.

—Operation Panel—

Figure 3:
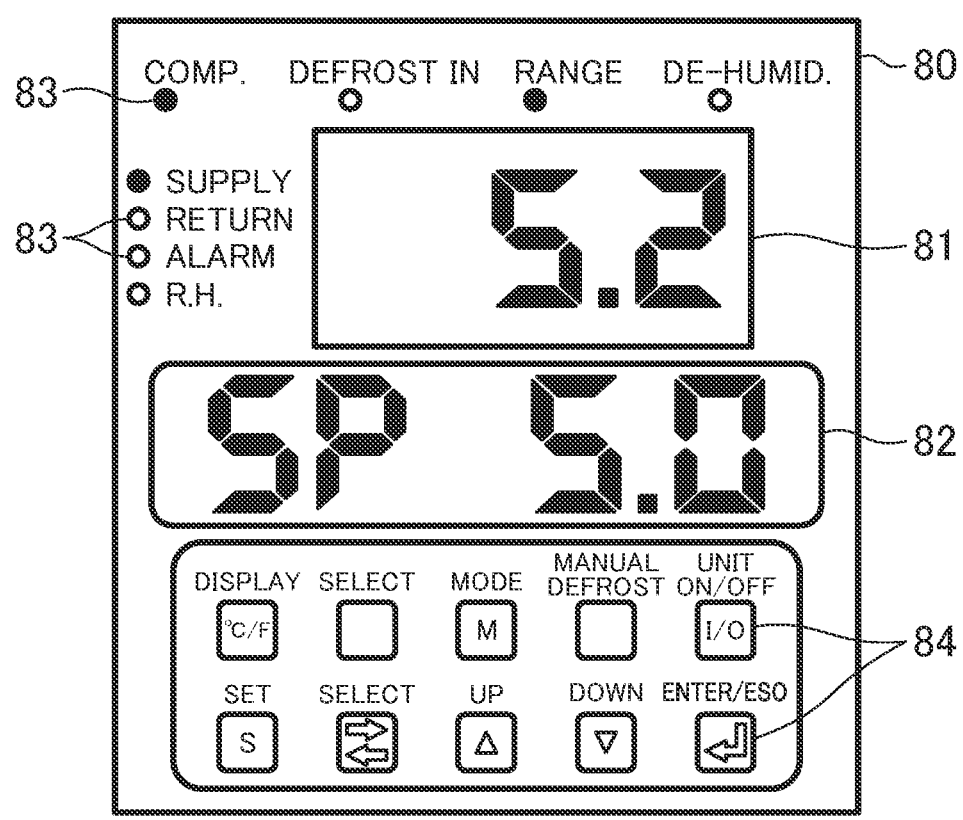
FIG. 3 is a front view of an operation panel of the internal environment control system.

As illustrated in FIG. 3, the operation panel (80) includes an ED display (81), a liquid crystal display (82), a plurality of display lamps (83), and a plurality of operation buttons (84). Although not shown in FIG. 1, the operation panel (80) is disposed on an outer side surface of the casing (30). The operation panel (80) is a notification device that notifies a human, such as an operator, of information.

The LED display (81), the liquid crystal display (82), and the display lamps (83) show information about the environment inside the cargo space (5) and information about the operating state of the internal environment control system (10). The operation buttons (84) constitute an input unit through which a human, such as an operator, inputs information to the internal environment control system (10). A human, such as an operator, operates the operation buttons (84) to input, for example, set values of temperature, an oxygen concentration, and a carbon dioxide concentration of the air in the cargo space (5), to the internal environment control system (10).

—State Index Sensors—

The state index sensors (15) are sensors each measures a state index, which is a physical quantity indicating the state of the target articles (7). The state index sensors (15) are state detectors.

Each state index sensor (15) measures the intensity of chlorophyll fluorescence emitted by the target articles (7) as the state index. The intensity of chlorophyll fluorescence is a physical quantity correlated with the state of photosynthesis by the fresh produce which is the target articles (7). A pulse modulation fluorometer can be used as the state index sensor (15).

As illustrated in FIG. 1, the internal environment control system (10) of the present embodiment includes a plurality of (three in FIG. 1) state index sensors (15). The state index sensors (15) are respectively provided for a plurality of (three in FIG. 1) cargos (6) placed at different positions.

—Controller—

As illustrated in FIG. 4, the controller (50) includes an arithmetic unit (60), a memory unit (70), and a communication unit (75).

<Arithmetic Unit>

The arithmetic unit (60) is, for example, a microprocessor comprised of an integrated circuit. The arithmetic unit (60) executes programs stored in the memory unit (70) to function as a refrigeration apparatus control unit (61), an air composition adjustment unit (62), a component diagnosis unit (63), a quality determination unit (64), and a log data generator (65).

The refrigeration apparatus control unit (61) controls the operation of components of the container refrigeration apparatus (20). For example, the refrigeration apparatus control unit (61) controls the operating capacity of the compressor (22) of the container refrigeration apparatus (20) so that the temperature of the cargo space (5) (temperature in the container) reaches a temperature set value. In this case, the refrigeration apparatus control unit (61) reduces the operating capacity of the compressor (22) when a measurement of the blowout temperature sensor (38) is lower than the temperature se value, and increases the operating capacity of the compressor (22) when the measurement of the blowout temperature sensor (38) is higher than the temperature set value.

The air composition adjustment unit (62) controls the air composition adjustment apparatus (40) so that the oxygen concentration and carbon dioxide concentration of the air in the cargo space (5) reach the respective set concentrations. The air composition adjustment unit (62) causes the air composition adjustment apparatus (40) to perform, for example: an operation of supplying the modified air (low oxygen concentration air) to the cargo space (5) to lower the oxygen concentration of the air in the cargo space (5); an operation of supplying the outside air to the cargo space (5) to raise the oxygen concentration of the air in the cargo space (5); and an operation of supplying the modified air (low oxygen concentration air) to the cargo space (5) while discharging the air from the cargo space (5) to lower the carbon dioxide concentration of the air in the cargo space (5).

The component diagnosis unit (63) diagnoses whether the components of the container refrigeration apparatus (20) and the air composition adjustment apparatus (40), which constitute the environment adjustment apparatus (14), operate normally. Specifically, the component diagnosis unit (63) diagnoses whether the compressor (22), expansion valve (24), internal fan (27), and external fan (26) of the container refrigeration apparatus (20) operate normally. The component diagnosis unit (63) also diagnoses whether the oxygen concentration sensor (47), the carbon dioxide concentration sensor (48), the suction temperature sensor (37), the blowout temperature sensor (38), and the evaporator temperature sensor (39) function normally. The component diagnosis unit (63) further diagnoses whether the amount of refrigerant filling the refrigerant circuit (21) is insufficient and whether the amount of frost adhering to the evaporator (25) is excessive.

The quality determination unit (64) determines whether there is a sign of degradation of the target articles contained in the cargo space. The quality determination unit (64) is a main processing unit of the quality determination apparatus (13).

The log data generator (65) acquires the measurements of the oxygen concentration sensor (47), the carbon dioxide concentration sensor (48), the suction temperature sensor (37), the blowout temperature sensor (38), and the evaporator temperature sensor (39) every predetermined time (e.g., 60 minutes), and transmits the acquired measurements to the memory unit (70).

<Memory Unit>

The memory unit (70) is, for example, a semiconductor memory comprised of an integrated circuit. The memory unit (70) stores programs for causing the controller (50) to execute predetermined operations and data necessary for the operations of the controller (50). The memory unit (70) functions as a set value storage (71), a reference value storage (72), and a log data storage (73).

The set value storage (71) stores user-set values of the temperature, oxygen concentration, and carbon dioxide concentration of the air in the cargo space (5). An operator presses the operation buttons (84) on the operation panel (80) to enter these user-set values to the controller (50).

The reference value storage (72) stores a reference fluorescence intensity related to the intensity of chlorophyll fluorescence. The quality determination unit (64) sets the reference fluorescence intensity.

The log data storage (73) stores, as log data, time-series data of the measurements of the sensors (37, 38, 39, 47, 48) transmitted from the log data generator (65).

<Communication Unit>

The communication unit (75) is configured to perform wired communication with the container refrigeration apparatus (20), the air composition adjustment apparatus (40), and the state index sensors (15). The communication unit (75) receives the measurements of the suction temperature sensor (37), the blowout temperature sensor (38), the evaporator temperature sensor (39), the oxygen concentration sensor (47), the carbon dioxide concentration sensor (48), and the state index sensors (15), and transmits the received measurements to the arithmetic unit (60). The communication unit (75) outputs command signals generated by the refrigeration apparatus control unit (61), the air composition adjustment unit (62), and the component diagnosis unit (63). The communication unit (75) of the present embodiment is a state acquisition unit that acquires a state index (the intensity of chlorophyll fluorescence in the present embodiment) measured by the state index sensors (15).

—Operation of Controller—

Operations performed by the quality determination unit (64) of the controller (50) will be described below. The quality determination unit (64) performs a reference setting operation for setting a reference fluorescence intensity and a main operation for determining whether there is a sign of degradation of the target articles (7). The quality determination unit (64) performs, as the main operation, a cause identification operation, a notification operation, a diagnosis instruction operation, and an environment change operation.

<Reference Setting Operation>

The reference setting operation performed by the quality determination unit (64) will be described reference to the flowchart of FIG. 5. In this reference setting operation, the quality determination unit (64) extremely lowers the oxygen concentration of the air in the cargo space (5) to apply stress to the fresh produce which is the target articles (7), and sets the reference fluorescence intensity based on the intensity of chlorophyll fluorescence of the target articles (7) under stress.

(Step ST11)

In Step ST11, the quality determination unit (64) defines the temperature set value to "a temperature at which no chilling injury of the target articles (7) occurs." The "temperature at which no chilling injury of the target articles (7) occurs" is a value predetermined for each kind of the target articles (7). For example, if the target articles (7) are "apples," the "temperature at which no chilling injury of the target articles (7) occurs" is 10° C.

In Step ST11, the quality determination unit (64) transmits the temperature set value, which is set to "the temperature at which no chilling injury of the target articles (7) occurs," to the refrigeration apparatus control unit (61). The refrigeration apparatus control unit (61) controls the operation of the container refrigeration apparatus (20) using the temperature set value transmitted from the quality determination unit (64).

In Step ST11, the quality determination unit (64) starts a protection condition timer. The protection condition timer measures time elapsed from a start point.

(Step ST12)

In the subsequent Step ST12, the quality determination unit (64) determines whether the temperature of the cargo space (5) is stable, Specifically, the quality determination unit (64) determines whether a stability condition that "the measurement of the blowout temperature sensor (38) remains within the range of the temperature set value±1° C. for one hour or longer" is met. The "temperature set value" of the stability condition is a value set in the processing of Step ST11.

When the stability condition is met, the quality determination unit (64) performs the processing of Step ST13. When the stability condition is not met, the quality determination unit (64) continues the processing of Step ST12.

(Step ST13)

In the processing of Step ST13, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value A.

The quality determination unit (64) of the present embodiment acquires the measurements of the intensity of chlorophyll fluorescence from the three state index sensors (15). Then, the quality determination unit (64) stores an arithmetic mean of the measurements acquired from the three state index sensors (15) as the stored value A in the memory unit (70).

(Step ST14)

In the processing of the subsequent Step ST14, the quality determination unit (64) determines an oxygen concentration set value and a carbon dioxide concentration set value to "0%." The quality determination unit (64) transmits the oxygen concentration set value and the carbon dioxide concentration set value, both set to "0%," to the air composition adjustment unit (62). The air composition adjustment unit (62) controls the operation of the air composition adjustment apparatus (40) using the oxygen concentration set value and the carbon dioxide concentration set value received from the quality determination unit (64).

The carbon dioxide concentration set value defined in the processing of Step ST14 does not have to be "0%," and may be a user-set value stored in the set value storage (71) of the memory unit (70).

(Step ST15)

In the processing of the subsequent Step ST15, the quality determination unit (64) waits for a predetermined time T1 (T1=60 minutes in the present embodiment). Until the time T1 elapses, the air composition adjustment apparatus (40) continues the operation for reducing the oxygen concentration of the air in the cargo space (5). As a result, the oxygen concentration of the air in the cargo space (5) drops to a value close to 0%, and stress is applied to the fresh produce which is the target articles (7).
(Step ST16)

In the processing of the subsequent Step ST16, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value B.

In the processing of Step ST16, the quality determination unit (64) calculates an arithmetic mean of the measurements acquired from the three state index sensors (15), as in the processing of Step ST13. Then, the quality determination unit (64) stores the arithmetic mean of the measurements of the three state index sensors (15) as the stored value B in the memory unit (70).
(Step ST17)

In the processing of the subsequent Step ST17, the quality determination unit (64) reads the stored values A and B from the memory unit (70), and determines whether the relationship "stored value B/stored value A≥104%" is met. The quality determination unit (64) determines whether the intensity of chlorophyll fluorescence has increased by a certain degree or more due to the stress applied to the target articles (7) by the reduction of the oxygen concentration of the air in the cargo space (5).

When the relationship "stored value B/stored value A≥104%" is met, the quality determination unit (64) performs the processing of Step ST18. When the relationship "stored value B/stored value A≥104%" is not met, the quality determination unit (64) performs the processing of Step ST20.
(Step ST18)

In the processing of Step ST18, the quality determination unit (64) sets 99% of the stored value B as the reference fluorescence intensity (reference fluorescence intensity=0.99×stored value B). The quality determination unit (64) stores 99% of the stored value B as the reference fluorescence intensity in the reference value storage (72) of the memory unit (70).

When the fresh produce is stored for a long period of time (e.g., several months), the function of chlorophyll (chloroplasts) of the fresh produce decreases as the fresh produce goes bad over time, which gradually lowers the intensity of chlorophyll fluorescence. For this reason, when the stored value B is set as the reference fluorescence intensity, the intensity of chlorophyll fluorescence of the fresh produce stored for a long time may fail to reach the reference fluorescence intensity when stressed by the low oxygen concentration. Thus, in Step ST18, the reference fluorescence intensity is set to a value slightly smaller than the stored value B.
(Step ST19)

In the subsequent Step ST19, the quality determination unit (64) resets the temperature set value, the oxygen concentration set value, and to carbon dioxide concentration set value to the corresponding user-set values stored in the set value storage (71) of the memory unit (70). When the processing of Step ST19 ends, the quality determination unit (64) ends the reference setting operation.
(Step ST20)

In the processing of Step ST20, the quality determination unit (64) determines whether a protection condition for protecting the target articles (7) from low oxygen concentration injury is met. The protection condition is a condition that at least one of a first sub-condition or a second sub-condition is met. The first sub-condition is a condition that "the measurement of the oxygen concentration sensor (47) remains less than the user-set value" for 24 hours or more.

The second sub-condition is a condition that "the measurement of the oxygen concentration sensor (47) remains less than 1%" for six hours or more.

When the protection condition is met, the quality determination unit (64) performs the processing of Step ST21. When the protection condition is not met, the quality determination unit (64) performs the processing after Step ST15 again.
(Step ST21)

In the processing of Step ST21, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value B.

In the processing of Step ST21, the quality determination unit (64) calculates an arithmetic mean of the measurements acquired from the three state index sensors (15) as the stored value B in the memory unit (70), as in the processing of Step ST16. The quality determination unit (64) updates the stored value B stored in the memory unit (70) from the value calculated in the processing of Step ST16 to the value calculated in Step ST21.
(Step ST22)

In the processing of the subsequent Step ST22, the quality determination unit (64) reads the stored values A and B from the memory unit (70), and determines whether the relationship "stored value B/stored value A≥102%" is met. The quality determination unit (64) determines whether the intensity of chlorophyll fluorescence has increased even a little due to the stress applied to the target articles (7) by the reduction of the oxygen concentration of the air in the cargo space (5).

When the relationship "stored value B/stored value A≥102%" is met, the quality determination unit (64) performs the processing of Steps ST18 and ST19. When the relationship "stored value B/stored value A≥102%" is not met, the quality determination unit (64) performs the processing of Step ST23.
(Step ST23)

When the relationship "stored value B/stored value A≥102%" is not met in the processing of Step ST22, the intensity of chlorophyll fluorescence of the fresh produce hardly increases even if the oxygen concentration of the air in the cargo space (5) is extremely lowered to apply stress to the fresh produce which is the target articles (7). In this case, the reference fluorescence intensity used to determine whether a sign condition (the condition indicating the sign of the degradation of the target articles (7)) is met cannot be set. Thus, in the processing of Step ST23, the quality determination unit (64) does not set the value of the reference fluorescence intensity, and prohibits the execution of the main operation. When the processing of Step ST23 ends, the quality determination unit (64) performs the processing of Step ST19.

<Main Operation>

The main operation performed by the quality determination unit (64) will be described with reference to the flowchart of FIG. 6.
(Step ST31)

In the processing of Step ST31, the quality determination unit (64) sets the temperature set value, the oxygen concentration set value, and the carbon dioxide concentration set value to the user-set values stored in the set value storage (71) of the memory unit (70).

The quality determination unit (64) transmits the temperature set value to the refrigeration apparatus control unit (61). The refrigeration apparatus control unit (61) controls the operation of the container refrigeration apparatus (20) using the temperature set value transmitted from the quality determination unit (64). Further, the quality determination unit (64) transmits the oxygen concentration set value and the carbon dioxide concentration set value to the air composition adjustment unit (62). The air composition adjustment unit (62) controls the operation of the air composition adjustment apparatus (40) using the oxygen concentration set value and the carbon dioxide concentration set value transmitted from the quality determination unit (64).

(Step ST32)

In the processing of the subsequent Step ST32, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value C.

Figure 5:
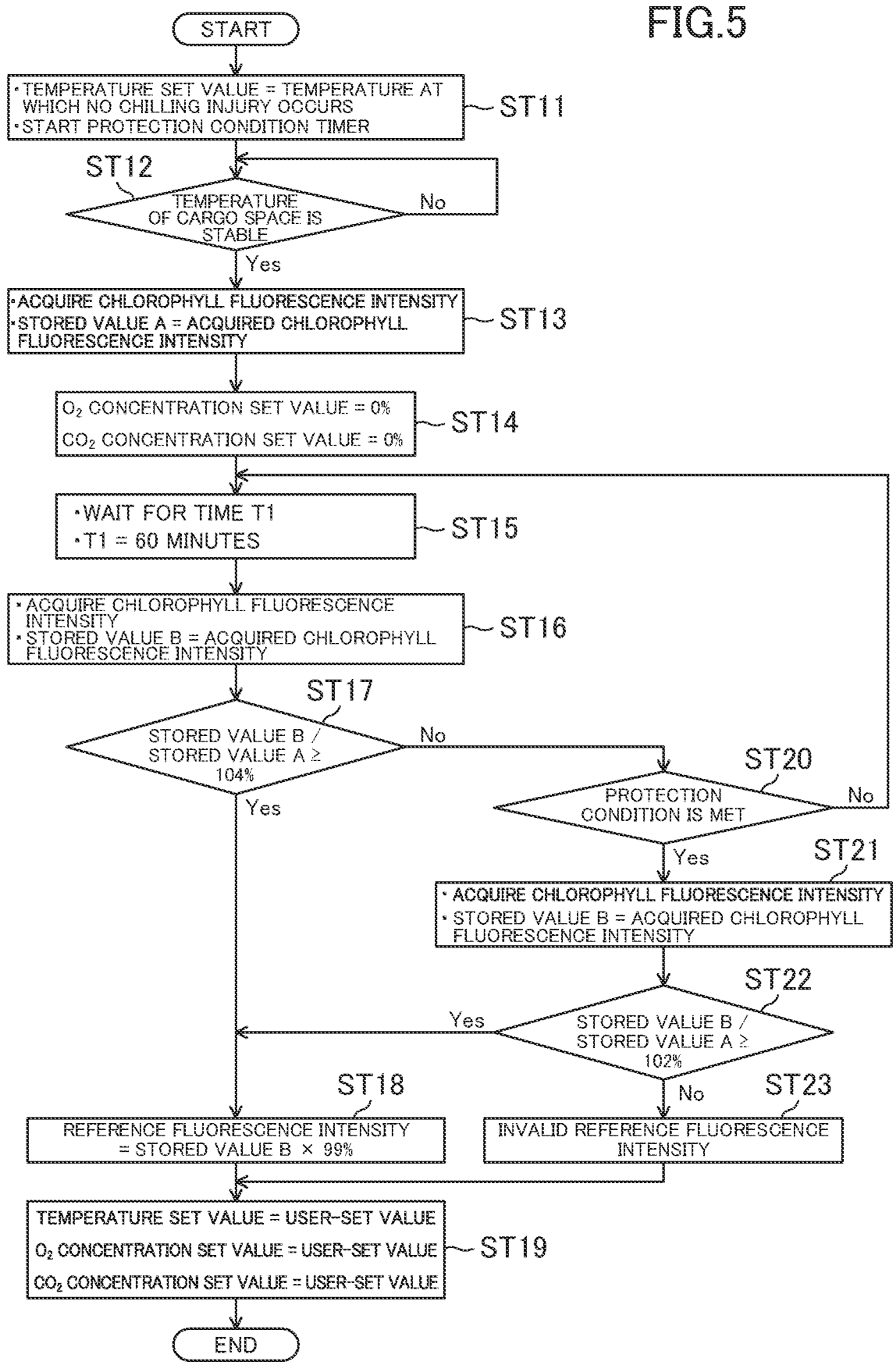
FIG. 5 is a flowchart illustrating a reference setting operation performed by a quality determination unit of a controller according to a first embodiment.

In the processing of Step ST32, the quality determination unit (64) calculates an arithmetic mean of the measurements acquired from the three state index sensors (15), as in the processing of Step ST13 shown in FIG. 5. Then, the quality determination unit (64) stores the arithmetic mean of the measurements of the three state index sensors (15) as the stored value C in the memory unit (70).

(Step ST33)

In the processing of the subsequent Step ST33, the quality determination unit (64) reads the stored value C from the memory unit (70) in Step ST32 and the reference fluorescence intensity stored in the reference value storage (72) of the memory unit (70). Then, the quality determination unit (64) determines whether the condition that "the reference value C is equal to or greater than the reference fluorescence intensity (reference value C≥reference fluorescence intensity)" is met.

When the reference value C is equal to or greater than the reference fluorescence intensity, the target articles (7) contained in the cargo space (5) are presumed to be under a relatively large stress. When the target articles (7) keep receiving such a relatively large stress, the target articles (7) are gradually degraded. Thus, the condition "reference value C≥reference fluorescence intensity" is a sign condition indicating the sign of degradation of the target articles (7) contained in the cargo space (5). The processing of Step ST33 is a determination operation for determining whether the sign condition is met.

When the condition "reference value C≥reference fluorescence intensity" is met, the quality determination unit (64) performs the processing of Step ST35. When the condition "reference value C≥reference fluorescence intensity" is not met, the quality determination unit (64) performs the processing of Step ST34.

(Step ST34)

When the reference value C is less than the reference fluorescence intensity, it is presumed that no large stress is applied to the target articles (7) and the quality of the target articles (7) is maintained. Thus, in the processing of Step ST34, the quality determination unit (64) waits for a predetermined time T2 (T2=180 minutes in the present embodiment). During standby of the quality determination unit (64), the refrigeration apparatus control unit (61) controls the container refrigeration apparatus (20) using the temperature set value defined in Step ST31, and the air composition adjustment unit (62) controls the air composition adjustment apparatus (40) using the oxygen concentration set value and the carbon dioxide concentration set value defined in Step ST31.

(Step ST35)

In the processing of Step ST35, the quality determination unit (64) calculates average values of the measurements of the oxygen concentration sensor (47), the carbon dioxide concentration sensor (48), the suction temperature sensor (37), the blowout temperature sensor (38), and the evaporator temperature sensor (39).

Specifically, the quality determination unit (64) reads time-series data for the last day from the time-series data of the measurements of the sensors (37, 38, 39, 47, 48) stored in the log data storage (73) of the memory unit (70). Then, the quality determination unit (64) calculates an arithmetic mean of the time-series data for one day of the measurements of the sensors (37, 38, 39, 47, 48).

(Step ST36)

In the processing of the subsequent Step ST36, the quality determination unit (64) performs a cause identification operation. The cause identification operation is an operation of identifying, from a plurality of environmental indexes indicating the internal environment of the storage space (5), an environmental index that causes the sign of degradation of the target articles (7).

For the cause identification operation, the quality determination unit (64) identifies a physical quantity that meets the sign condition from the physical quantities measured by the oxygen concentration sensor (47), the carbon dioxide concentration sensor (48), the suction temperature sensor (37), the blowout temperature sensor (38), and the evaporator temperature sensor (39), and regards the identified physical quantity as a causal environmental index.

Specifically, in the processing of Step ST36, the quality determination unit (64) acquires the measurements of the sensors (37, 38, 39, 47, 48) as the current values. Next, the quality determination unit (64) calculates a difference between the "average value calculated in Step ST35" and the "current value acquired in Step ST36" for each of the measurements of the sensors (37, 38, 39, 47, 48), and sets the difference as a determination value (determination value=average value−current value). Then, the quality determination unit (64) specifies the causal environmental index based on the determination value for each sensor (37, 38, 39, 47, 48). Note that the causal environmental index specified by the cause identification operation performed once may be a single physical quantity or plural physical quantities.

For example, when the determination value for the measurement of the oxygen concentration sensor (47) is less than a predetermined reference value, the current value of the oxygen concentration of the air in the cargo space (5) is significantly lower than the average value. Thus, the excessively low oxen concentration is presumed to degrade the target articles (7). Thus, in this case, the quality determination unit (64) regards the oxygen concentration of the air in the cargo space (5) measured by the oxygen concentration sensor (47) as the causal environmental index.

When the determination value for the measurement of the carbon dioxide concentration sensor (48) is greater than a predetermined reference value, the current value of the carbon dioxide concentration of the air in the cargo space (5) is significantly greater than the average value. Thus, the excessively high carbon dioxide concentration is presumed to degrade the target articles (7). In this case, the quality determination unit (64) regards the carbon dioxide concentration of the air in the cargo space (5) measured by the carbon dioxide concentration sensor (48) as the causal environmental index.

When the determination value for the measurement of the suction temperature sensor (37) is less than a predetermined reference value, the current value of the temperature of the air in the cargo space (5) is significantly less than the average value. Thus, the excessively low temperature of the cargo space (5) is presumed to degrade the target articles (7). In this case, the quality determination unit (64) regards the temperature of the air in the cargo space (5) measured by the suction temperature sensor (37) as the causal environmental index.

(Step ST37)

In the processing of the subsequent Step ST37, the quality determination unit (64) performs a notification operation and a diagnosis instruction operation.

The notification operation is an operation of instructing the operation panel (80), which is a notification device, to notify the possibility of degradation of the target articles (7). For the notification operation, the quality determination unit (64) transmits, to the operation panel (80) via the communication unit (75), a notification instruction signal instructing presentation of information indicating the possibility of degradation of the target articles (7).

Receiving the notification instruction signal, the operation panel (80) displays the information indicating the possibility of degradation of the target articles (7) on the LED display (81) or the liquid crystal display (82). Then, a human, such as an operator, is notified of the information indicating the possibility of degradation of the target articles (7).

The diagnosis instruction operation is an operation of instructing the environment adjustment apparatus (14) to diagnose whether the components of the environment adjustment apparatus (14) function normally. For the diagnosis instruction operation, the quality determination unit (64) transmits a diagnosis instruction signal instructing the execution of the diagnosis operation to the component diagnosis unit (63).

Receiving the diagnosis instruction signal, the component diagnosis unit (63) diagnoses whether the components of the container refrigeration apparatus (20) and the air composition adjustment apparatus (40), which constitute the environment adjustment apparatus (14), operate normally. Then, the component diagnosis unit (63) transmits the diagnosis result to the quality determination unit (64).

(Step ST38)

In the processing of the subsequent Step ST38, the quality determination unit (64) performs the processing of Step ST39 when the diagnosis result received from the component diagnosis unit (63) indicates that the components of the container refrigeration apparatus (20) and the air composition adjustment apparatus (40) operate normally. When the diagnosis result received from the component diagnosis unit (63) does not indicate that the components of the container refrigeration apparatus (20) and the air composition adjustment apparatus (40) operate normally, the quality determination unit (64) ends the main operation.

(Step ST39)

In the processing of Step ST39, the quality determination unit (64) performs an environment change operation. The environment change operation is an operation of instructing the environment adjustment apparatus (14) to change the internal environment of the storage space (5) in order to keep the target articles (7) from degradation.

For the environment change operation, the quality determination unit (64) transmits signals to the refrigeration apparatus control unit (61) and the air composition adjustment unit (62) to instruct both units to change the "causal environmental index identified by the cause identification operation in Step ST36." When the processing of Step ST39 ends, the quality determination unit (64) ends the main operation.

For example, if "the oxygen concentration of the air in the cargo space (5)" is identified as the causal environmental index in Step S136 and the excessively low "oxygen concentration of the air in the cargo space (5)" is presumed to be the cause of the sign of degradation of the target articles (7), the quality determination unit (64) transmits a signal instructing the air composition adjustment unit (62) to increase the oxygen concentration set value by a predetermined value to the air composition adjustment unit (62). Receiving this signal, the air composition adjustment unit (62) controls the operation of the air composition adjustment apparatus (40) so that the measurement of the oxygen concentration sensor (47) reaches the increased oxygen concentration set value. This raises the oxygen concentration of the air in the cargo space (5), and keeps the target articles (7) in the cargo space (5) from degradation.

If the "carbon dioxide concentration of the air in the cargo space (5)" is identified as the causal environmental index in Step ST36 and the excessively high "carbon dioxide concentration of the air in the cargo space (5)" is presumed to be the cause of the sign of degradation of the target articles (7), the quality determination unit (64) transmits a signal instructing the air composition adjustment unit (62) to lower the carbon dioxide concentration set value by a predetermined value to the air composition adjustment unit (62). Receiving this signal, the air composition adjustment unit (62) controls the operation of the air composition adjustment apparatus (40) so that the measurement of the carbon dioxide concentration sensor (48) reaches the lowered carbon dioxide concentration set value. This lowers the carbon dioxide concentration of the air in the cargo space (5), and keeps the target articles (7) in the cargo space (5) from degradation.

If "the temperature of the air sucked from the cargo space (5) into the container refrigeration apparatus (20)" is identified as the causal environmental index in Step ST36 and the excessively low "temperature of the air in the cargo space (5)" is presumed to be the cause of the sign of degradation of the target articles (7), the quality determination unit (64) transmits a signal instructing the refrigeration apparatus control unit (61) to increase the temperature set value by a predetermined value to the refrigeration apparatus control unit (61). Receiving this signal, the refrigeration apparatus control unit (61) controls the operation of the container refrigeration apparatus (20) so that the measurement of the blowout temperature sensor (38) reaches the increased temperature set value. This raises the temperature of the air in the cargo space (5), and keeps the target articles (7) in the cargo space (5) from degradation.

If a large amount of frost adheres to the evaporator (25), the evaporation temperature of the refrigerant in the evaporator (25) decreases, and the temperature of the air passing through the evaporator (25) decreases too much. This may excessively lower the temperature of the air in the cargo space (5). Thus, if the "temperature of the air sucked from the cargo space (5) into the container refrigeration apparatus (20)" is identified as the causal environmental index in Step ST36 and the excessively low "temperature of the air in the cargo space (5)" is presumed to be the cause of the sign of degradation of the target articles (7), the quality determination unit (64) may transmit a signal instructing the container refrigeration apparatus (20) to perform a defrosting operation for melting the frost adhering to the evaporator (25) to the container refrigeration apparatus (20) via the communication unit (75).

If the "temperature of the air blown from the container refrigeration apparatus (20) into the cargo space (5)" is identified as the causal environmental index in Step ST36 and the excessively low "temperature of the air in the cargo space (5)" is presumed to be the cause of the sign of quality deterioration of the target article (7), the quality determination unit (64) transmits a signal instructing the refrigeration apparatus control unit (61) to increase the blowout temperature set value by a predetermined value to the refrigeration apparatus control unit (61). Receiving this signal, the refrigeration apparatus control unit (61) controls the operation of the container refrigeration apparatus (20) so that the measurement of the blowout temperature sensor (38) reaches the increased blowout temperature set value. This raises the temperature of the air in the cargo space (5), and keeps the target articles (7) in the cargo space (5) from degradation.

As described above, a large amount of frost adhering to the evaporator (25) may excessively lower the temperature of the air in the cargo space (5). Thus, if the "temperature of the air blown from the container refrigeration apparatus (20) into the cargo space (5)" is identified as the causal environmental index in Step ST36 and the excessively low "temperature of the air in the cargo space (5)" is presumed to be the cause of the sign of degradation of the target articles (7), the quality determination unit (64) may transmit a signal instructing the container refrigeration apparatus (20) to perform the defrosting operation to the container refrigeration apparatus (20) via the communication unit (75).

If the "temperature of the evaporator (25)" is identified as the causal environmental index in Step ST36, a large amount of frost adheres to the evaporator (25). This may lower the temperature of the air in the cargo space (5) too much. In such a case, the quality determination unit (64) transmits a signal instructing the container refrigeration apparatus (20) to perform the defrosting operation to the container refrigeration apparatus (20) via the communication unit (75). In this case, the quality determination unit (64) may transmit a signal instructing the refrigeration apparatus control unit (61) to increase the temperature set value by a predetermined value to the refrigeration apparatus control unit (61).

—Feature (1) of First Embodiment—

The quality determination apparatus (13) of the present embodiment includes the state index sensors (15) and the quality determination unit (64). Each state index sensor (15) detects a state index. The state index is an index indicating the state of the target articles (7) contained in the cargo space (5) where the internal environment is controlled. The quality determination unit (64) performs the determination operation. The determination operation is an operation of determining whether the sign condition indicating the sign of degradation of the target articles (7) is met based on the state indexes detected by the state index sensors (15).

In the quality determination apparatus (13) of the present embodiment, the quality determination unit (64) performs the determination operation, thereby determining whether there is the sign of degradation of the target articles (7) based on the state indexes detected by the state index sensors (15). Thus, the quality determination apparatus (13) of the present embodiment is able to determine whether the target articles (7) actually contained in the cargo space (5) are degraded.

—Feature (2) of First Embodiment—

The quality determination unit (64) of the quality determination apparatus (13) of the present embodiment performs the environment change operation when determining that the sign condition is met. The environment change operation is the operation of instructing the environment adjustment apparatus (14) that adjusts the internal environment of the cargo space (5) to change the internal environment of the cargo space (5) in order to keep the target articles (7) from degradation.

The quality determination unit (64) of the quality determination apparatus (13) of the present embodiment performs the environment change operation when determining that the sign condition is met in the determination operation. In the environment change operation, the quality determination unit (64) instructs the environment adjustment apparatus (14) to change the internal environment of the cargo space (5). Receiving the instruction from the quality determination unit (64), the environment adjustment apparatus (14) changes the internal environment of the cargo space (5) in order to keep the target articles (7) from degradation. Thus, according to the present embodiment, the internal environment of the cargo space (5) can he made suitable for maintaining the quality of the target articles (7) actually contained in the cargo space (5). This can minimize the degradation of the target articles (7) during storage in the cargo space (5).

The quality determination unit (64) of the present embodiment performs the environment change operation when the sign condition indicating the sign of degradation of the target articles (7) is met. This can change the internal environment of the cargo space (5) to maintain the quality of the target articles (7) before the target articles (7) are seriously degraded. When the target articles (7) are degraded only slightly, the quality of the target articles (7) can be recovered by making the internal environment of the cargo space (5) suitable for storing the target articles (7). Thus, the quality determination apparatus (13) of the present embodiment can recover the quality of the target articles (7) by the environment change operation performed by the quality determination unit (64). This can maintain the quality of the target articles (7) high for a long period of time.

—Feature (3) of First Embodiment—

The quality determination unit (64) of the quality determination apparatus (13) of the present embodiment performs the cause identification operation when determining that the sign condition is met. The cause identification operation is the operation of identifying, from a plurality of environmental indexes indicating the internal environment of the cargo space (5), an environmental index that causes the sign of degradation of the target articles (7).

The quality determination unit (64) of the present embodiment performs the cause identification operation when determining that the sign condition is met in the determination operation. in the cause identification operation, the quality determination unit (64) identifies the environmental index that causes the sign of degradation of the target articles (7), and regards the identified environmental index as the causal environmental index.

The quality determination unit (64) of the present embodiment performs the environment change operation after the cause identification operation ends. In the environment change operation, the quality determination unit (64) controls the operation of the container refrigeration apparatus (20) or the air composition adjustment apparatus (40) so that the causal environmental index related to the air in the cargo space (5) reaches a value suitable for maintaining the quality of the target articles (7). Thus, according to the present embodiment, the environmental index, which causes the sign of the degradation of the target articles (7), can be set to a value suitable for maintaining the quality of the target articles (7), thereby reliably keeping the target articles (7) from degradation.

—Feature (4) of First Embodiment—

In the present embodiment, the quality determination unit (64) of the quality determination apparatus (13) performs the notification operation when determining that the sign condition is met. The notification operation is the operation of instructing the operation panel (80) which notifies a human of information to notify the possibility of degradation of the target articles (7).

The quality determination unit (64) of the present embodiment performs the notification operation when determining that the sign condition is met in the determination operation. In the notification operation, the quality determination unit (64) instructs the operation panel (80) to notify the possibility of degradation of the target articles (7). The operation panel (80) that has received the instruction from the quality determination unit (64) notifies a human, such as an operator, of information indicating the possibility of degradation of the target articles (7). Thus, the quality determination apparatus (13) of the present embodiment is able to notify a human of the possibility of degradation of the target articles (7).

—Feature (5) of First Embodiment—

The quality determination unit (64) of the present embodiment performs the diagnosis instruction operation when determining that the sign condition is met. The diagnosis instruction operation is the operation of instructing the environment adjustment apparatus (14) that adjusts the internal environment of the cargo space (5) to diagnose whether the components of the environment adjustment apparatus (14) function normally.

The quality determination unit (64) of the present embodiment performs the diagnosis instruction operation when determining that the sign condition is met in the determination operation. In the diagnosis instruction operation, the quality determination unit (64) instructs the environment adjustment apparatus (14) to diagnose whether the components of the environment adjustment apparatus (14) function normally. Receiving the instruction from the quality determination unit (64), the environment adjustment apparatus (14) diagnoses whether the components function normally Thus, according to the present embodiment, whether the cause of the degradation of the target articles (7) is a failure of any of the components of the environment adjustment apparatus (14) can be determined.

The quality determination unit (64) of the present embodiment performs the diagnosis instruction operation, and performs the environment change operation after confirming that the components of the environment adjustment apparatus (14) function normally. Thus, the quality determination apparatus (13) of the present embodiment can make the internal environment of the cargo space (5) suitable for storing the target articles (7), thereby maintaining the quality of the target articles (7).

—Feature (6) of First Embodiment—

In the quality determination apparatus (13) of the present embodiment, the state index sensor (15) detects, as the state index, the intensity of chlorophyll fluorescence of the fresh produce which is the target articles (7).

Chlorophyll fluorescence is an index of the state of photosynthesis by plants. The state index sensor (15) of the present embodiment detects the intensity of chlorophyll fluorescence as the state index.

—Feature (7) of First Embodiment—

For the quality determination unit (64) of the present embodiment, the sign condition is a condition that the intensity of chlorophyll fluorescence detected by the state index sensor (15) exceeds the reference fluorescence intensity. The quality determination unit (64) sets the reference fluorescence intensity based on the intensity of chlorophyll fluorescence detected by the state index sensor (15) when the oxygen concentration in the cargo space (5) is lowered.

The quality determination unit (64) of the present embodiment determines that the sign condition is met when the intensity of chlorophyll fluorescence detected by the state index sensor (15) exceeds the reference fluorescence intensity. When the oxygen concentration in the cargo space (5) decreases, the state of photosynthesis by the fresh produce which is the target articles (7) changes, thereby changing the intensity of chlorophyll fluorescence emitted by the target articles (7). Thus, the quality determination unit sets the reference fluorescence intensity based on the intensity of chlorophyll fluorescence measured when the oxygen concentration in the cargo space (5) is lowered.

Second Embodiment

A second embodiment will be described below. equality determination apparatus (13) of the present embodiment is a modified version of the quality determination apparatus (13) of the first embodiment in which the quality determination unit (64) of the controller (50) performs a modified reference setting operation. The following description of the quality determination apparatus (13) of the present embodiment will be focused on the differences from the quality determination apparatus (13) of the first embodiment.

—Operation of Controller—

Operations performed by the quality determination unit (64) of the controller (50) will be described below The quality determination unit (64) of the present embodiment performs the same main operation as the quality determination unit (64) of the first embodiment.

<Reference Setting Operation>

Figure 7:
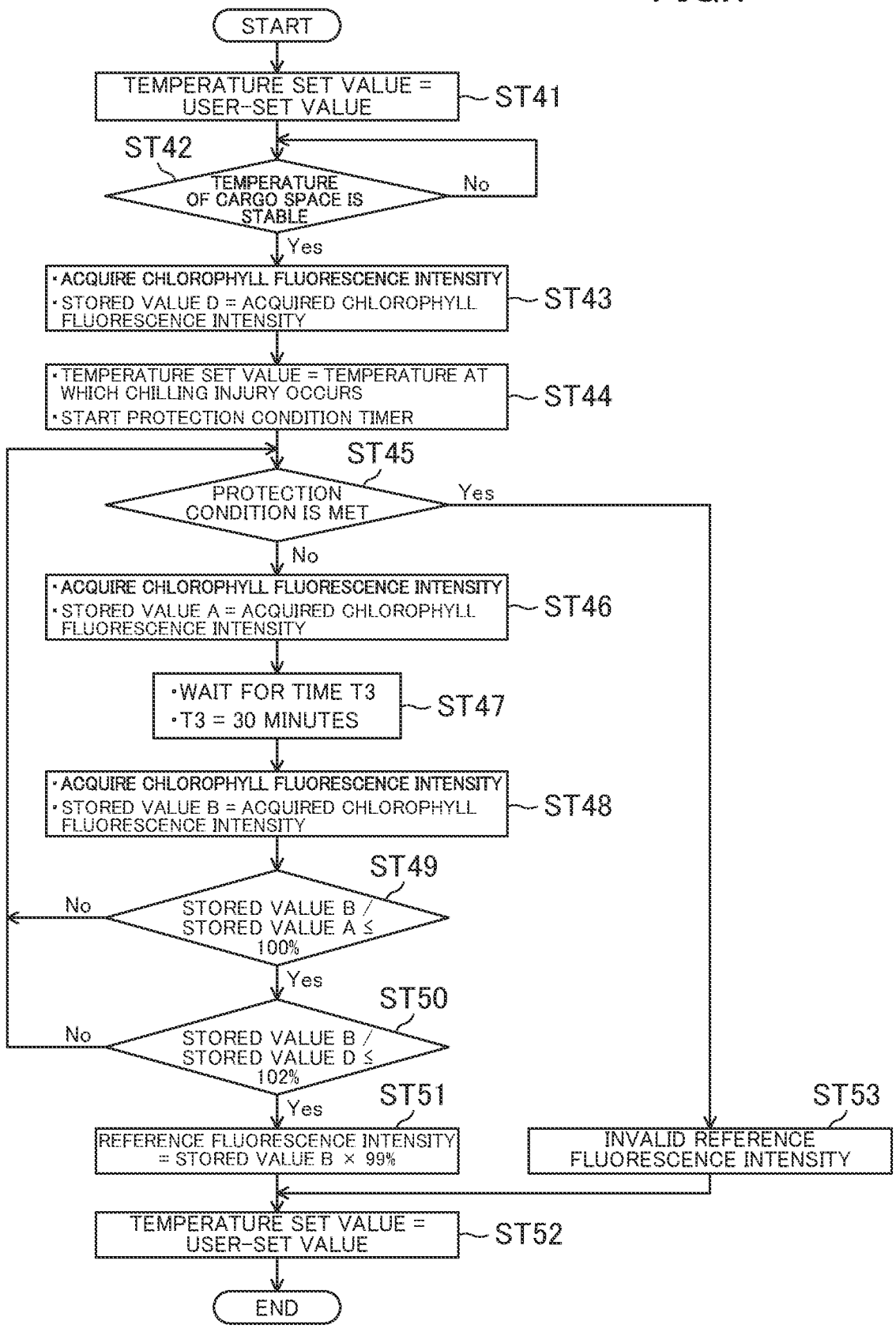
FIG. 7 is a flowchart illustrating a reference setting operation performed by a quality determination unit of a controller according to a second embodiment.

The reference setting operation performed by the quality determination unit (64) of the present embodiment will be described with reference to the flowchart shown in FIG. 7. In this reference setting operation, the quality determination unit (64) lowers the temperature of the air in the cargo space (5) to apply stress to the fresh produce which is the target articles (7), and sets the reference fluorescence intensity based on the intensity of chlorophyll fluorescence of the target articles (7) under stress.

(Step ST41)

In the processing of Step ST41, the quality determination unit (64) defines the temperature set value to a user-set temperature value of the cargo space (5) stored in the set value storage (71) of the memory unit (70).

The quality determination unit (64) transmits the temperature set value defined to the user-set value to the refrigeration apparatus control unit (61). The refrigeration apparatus control unit (61) controls the operation of the container refrigeration apparatus (20) using the temperature set value transmitted from the quality determination unit (64). Specifically, the refrigeration apparatus control unit (61) adjusts the cooling capability of the container refrigeration apparatus (20) so that the measurement of the blowout temperature sensor (38) reaches the temperature set value.

While the quality determination unit (64) of the present embodiment performs the reference setting operation, the air composition adjustment apparatus (40) is kept stopped.

Thus, during the execution of the reference setting operation, the air in the cargo space (5) has substantially the same composition as the atmospheric air.
(Step ST42)

In the subsequent Step ST42, the quality determination unit (64) determines whether the temperature of the cargo space (5) is stable. Specifically, the quality determination unit (64) determines whether a stability condition that "the measurement of the blowout temperature sensor (38) remains within the range of the temperature set value±1° C. for one hour or longer" is met. The "temperature set value" of the stability condition is a value set in the processing of Step ST41.

When the stability condition is met, the quality determination unit (64) performs the processing of Step ST43. When the stability condition is not met, the quality determination unit (64) continues the processing of Step ST42.

Until the stability condition is met, the container refrigeration apparatus (20) continues the operation of cooling the air in the cargo space (5) so that the measurement of the blowout temperature sensor (38) reaches the temperature set value set in Step ST41. As a result, the temperature of the air in the cargo space (5) approaches the user-set value.
(Step ST43)

In the processing of Step ST43, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value D. In the processing of Step ST43, the quality determination unit (64) calculates an arithmetic mean of the measurements acquired from the three state index sensors (15) as the stored value D in the memory unit (70), as in the processing of Step ST13 shown in FIG. 5.
(Step ST44)

In the processing of Step ST44, the quality determination unit (64) defines the temperature set value to "a temperature at which chilling injury of the target articles (7) occurs." The "temperature at which no chilling injury of the target articles (7) occurs" is a value predetermined for each kind of the target articles (7). For example, if the target articles (7) are "bananas," the "temperature that causes chilling injury of the target articles (7)" is 10° C.

In the processing of Step ST44, the quality determination unit (64) transmits the temperature set value, which is set to "the temperature at which no chilling injury of the target articles (7) occurs," to the refrigeration apparatus control unit (61). The refrigeration apparatus control unit (61) controls the operation of the container refrigeration apparatus (20) using the temperature set value transmitted from the quality determination unit (64). As a result, the temperature of the air in the cargo space (5) becomes relatively low, and stress is applied to the fresh produce which is the target articles (7).

In the processing of Step ST44, the quality determination unit (64) starts a protection condition timer. The protection condition timer measures time elapsed from a start point.
(Step ST45)

In the processing of Step ST45, the quality determination unit (64) determines whether a protection condition for protecting the target articles (7) from chilling injury is met. The protection condition is a condition that 24 hours or more have passed since the temperature set value was set to the "temperature at which chilling injury of the target articles (7) occurs."

When the protection condition is met, the quality determination unit (64) performs the processing of Step ST53.

When the protection condition is not met, the quality determination unit (64) performs the processing of Step ST46.
(Step ST46)

In the processing of Step ST46, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value A. In the processing of Step ST46, the quality determination unit (64) calculates an arithmetic mean of the measurements acquired from the three state index sensors (15) as the stored value A in the memory unit (70), as in the processing of Step ST43.
(Step ST47)

In the processing of the subsequent Step ST47, the quality determination unit (64) waits for a predetermined time T3 (T3=30 minutes in the present embodiment). During standby of the quality determination unit (64), the container refrigeration apparatus (20) continues the operation of cooling the air in the cargo space (5) so that the measurement of the blowout temperature sensor (38) reaches the temperature set value set in Step ST44. As a result, the temperature of the air in the cargo space (5) is kept relatively low, and stress is kept applied to the fresh produce which is the target articles (7).
(Step ST48)

In the processing of the subsequent Step ST48, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value B.

In the processing of Step ST48, the quality determination unit (64) calculates an arithmetic mean of the measurements acquired from the three state index sensors (15), as in the processing of Step ST43. Then, the quality determination unit (64) stores the arithmetic mean of the measurements of the three state index sensors (15) as the stored value B in the memory unit (70).
(Step ST49)

In the processing of the subsequent Step ST49, the quality determination unit (64) reads the stored values A and B from the memory unit (70), and determines whether the relationship "stored value B/stored value A≤100%" is met. The quality determination unit (64) determines whether the intensity of chlorophyll fluorescence of the target articles (7) has increased for the standby time T3 in Step ST47. When the relationship "stored value B/stored value A≤100%" is met, it can be presumed that the increase in chlorophyll fluorescence caused by the stress applied to the target articles (7) due to the lowered temperature of the air in the cargo space (5) has stopped.

When the relationship "stored value B/stored value A≤100%" is met, the quality determination unit (64) performs the processing of Step ST50. When the relationship "stored value B/stored value A≤100%" is not met, the quality determination unit (64) performs the processing after Step ST45 again.
(Step ST50)

In the processing of the subsequent Step ST50, the quality determination unit (64) reads the stored values B and D from the memory unit (70), and determines whether the relationship "stored value B/stored value D≤102%" is met. The quality determination unit (64) compares the stored value D, which is the intensity of chlorophyll fluorescence measured before lowering the temperature of the air in the cargo space (5) to apply the stress to the target articles (7), with the stored value B, which is the intensity of chlorophyll fluorescence measured after lowering the temperature of the air in the cargo space (5) to apply the stress to the target articles (7). Then, the quality determination unit (64) determines whether the intensity of chlorophyll fluorescence has increased by a certain degree or more by applying the stress to the target articles (7).

When the relationship "stored value B/stored value D≤102%" is met in the processing of Step ST50, the relationship "stored value B/stored value A≤100%" is met in Step ST49 and the relationship "stored value B/stored value D≤102%" is met in Step ST50. Thus, in this case, it can be presumed that applying the stress to the target articles (7) has increased the intensity of chlorophyll fluorescence to some extent or more, and the increase in the intensity of chlorophyll fluorescence due to the stress has already stopped.

Thus, when the relationship "stored value B/stored value D≤102%" is met, the quality determination unit (64) performs the processing of Step ST51. When the relationship "stored value B/stored value D≤102%" is not met, the quality determination unit (64) performs the processing after Step ST45 again.

(Step ST51)

In the processing of Step ST51, the quality determination unit (64) sets 99% of the stored value B as the reference fluorescence intensity (reference fluorescence intensity=0.99×stored value B). The quality determination unit (64) stores 99% of the stored value B as the reference fluorescence intensity in the reference value storage (72) of the memory unit (70). The reason why the value of 99% of the stored value B is set as the reference fluorescence intensity is the same as the reason described for Step ST18 shown in FIG. 5.

(Step ST52)

In the processing of the subsequent Step ST52, the quality determination unit (64) defines the temperature set value to the user-set value of the temperature stored in the set value storage (71) of the memory unit (70). When the processing of Step ST52 ends, the quality determination unit (64) ends the reference setting operation.

(Step ST53)

When the protection condition is met in the processing of Step ST45, the intensity of chlorophyll fluorescence of the fresh produce hardly increases even if the temperature of the air in the cargo space (5) is extremely lowered to apply stress to the fresh produce which is the target articles (7). In this case, the reference fluorescence intensity used to determine whether a sign condition (the condition indicating the sign of the degradation of the target articles (7)) is met cannot be set. Thus, in the processing of Step ST53, the quality determination unit (64) does not set the value of the reference fluorescence intensity, and prohibits the execution of the main operation. When the processing of Step ST53 ends, the quality determination unit (64) performs the processing of Step ST52.

Third Embodiment

A third embodiment will be described below. A quality determination apparatus (13) of the present embodiment is a modified version of the quality determination apparatus (13) of the first embodiment in which the quality determination unit (64) of the controller (50) performs a modified operation. The following description of the quality determination apparatus (13) of the present embodiment will be focused on the differences from the quality determination apparatus (13) of the first embodiment.

—Operation of Controller—

Operations performed by the quality determination unit (64) of the controller (50) will be described below. The quality determination unit (64) of the present embodiment performs the main operation, and performs no reference setting operation.

<Main Operation>

Figure 8:
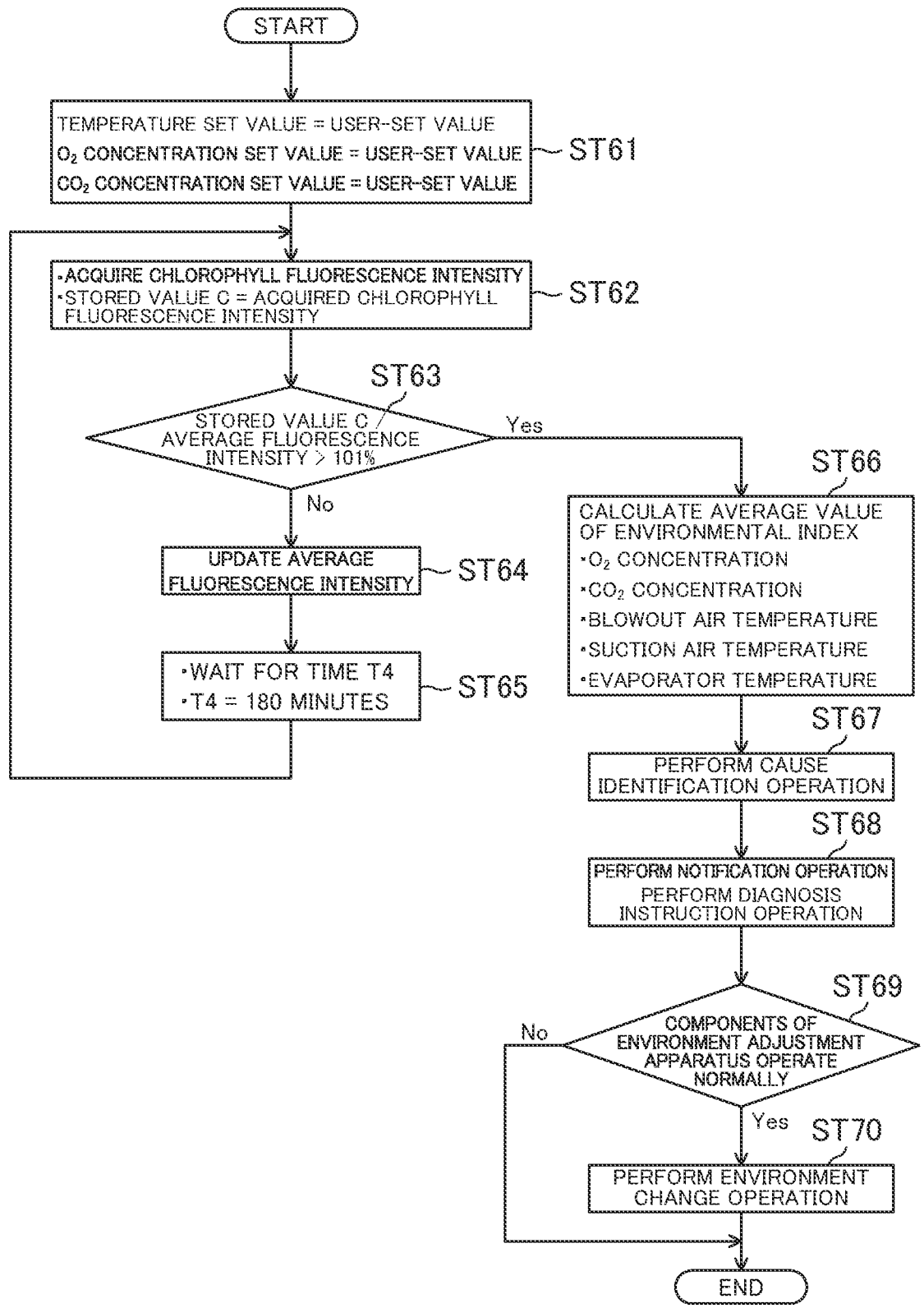
FIG. 8 is a flowchart illustrating a main operation performed by a quality determination unit of a controller according to a third embodiment.

The main operation performed by the quality determination unit (64) of the present embodiment will be described with reference to the flowchart shown in FIG. 8. In this main operation, the quality determination unit (64) monitors the intensity of chlorophyll fluorescence of the fresh produce which is the target articles (7), and determines that the target articles (7) show the sign of degradation when the intensity of chlorophyll fluorescence has increased to some extent.

(Step ST61)

In the processing of Step ST61, the quality determination unit (64) defines the temperature set value, the oxygen concentration set value, and the carbon dioxide concentration set value to the corresponding user-set values stored in the set value storage (71) of the memory unit (70).

The quality determination unit (64) transmits the temperature set value to the refrigeration apparatus control unit (61). The refrigeration apparatus control unit (61) controls the operation of the container refrigeration apparatus (20) using the temperature set value transmitted from the quality determination unit (64). Further, the quality determination unit (64) transmits the oxygen concentration set value and the carbon dioxide concentration set value to the air composition adjustment unit (62). The air composition adjustment unit (62) controls the operation of the air composition adjustment apparatus (40) using the oxygen concentration set value and the carbon dioxide concentration set value transmitted from the quality determination unit (64).

(Step ST62)

In the processing of the subsequent Step ST62, the quality determination unit (64) acquires the intensity of chlorophyll fluorescence measured by the state index sensors (15). The quality determination unit (64) stores the acquired measurements of the intensity of chlorophyll fluorescence in the memory unit (70) as a stored value C. In the processing of Step ST62, the quality determination unit (64) calculates an arithmetic mean of the measurements acquired from the three state index sensors (15) as the stored value C in the memory unit (70), as in the processing of Step ST32 shown in FIG. 6.

(Step ST63)

In the processing of the subsequent Step ST63, the quality determination unit (64) reads the stored value C and an average fluorescence intensity from the memory unit (70), and determines whether the relationship "stored value C/average fluorescence intensity>101%" is met. The quality determination unit (64) determines whether the intensity of chlorophyll fluorescence of the fresh produce stored as the target articles (7) in the cargo space (5) has increased. The average fluorescence intensity will be described later.

When the reference value C is greater than 101% of the average fluorescence intensity, the target articles (7) contained in the cargo space (5) are presumed to be under stress. The target articles (7) kept wider stress are gradually degraded. Thus, the condition "stored value C/average fluorescence intensity>101%" is a sign condition indicating the sign of degradation of the target articles (7) contained in the cargo space (5). The processing of Step ST63 is a determination operation for determining whether the sign condition is met.

When the relationship "stored value C/average fluorescence intensity>101%" is met, the quality determination unit

(64) performs the processing of Step ST66. When the relationship "stored value C/average fluorescence intensity>101%" is not met, the quality determination unit (64) performs the processing of Step ST64.

(Step ST64)

In the processing of Step ST64, the quality determination unit (64) updates the average fluorescence intensity and stores the updated average fluorescence intensity in the memory unit (70).

In the main operation of the present embodiment, the quality determination unit (64) performs the processing from Steps ST62 to ST65 multiple times. The quality determination unit (64) acquires the stored value C every time the processing of Step ST62 is performed, and stores an arithmetic mean of the plurality of stored values C acquired so far as the average fluorescence intensity in the memory unit (70).

Specifically, the stored value C acquired by the quality determination unit (64) in the processing of the N-th Step ST62 is referred to as "C(n)." In the N-th Step ST64, the quality determination unit (64) performs the calculation represented by the following formula to calculate the average fluorescence intensity.

Average fluorescence intensity=$(C(1)+C(2)+C(3)+\ldots+C(N-1)+C(N))/N$ (Step ST65)

In the processing of the subsequent Step ST65, the quality determination unit (64) waits for a predetermined time T4 (T4=180 minutes in the present embodiment). When the processing of Step ST65 ends, the quality determination unit (64) performs the processing after Step ST62 again.

(Steps ST66 to ST170)

Figure 6:
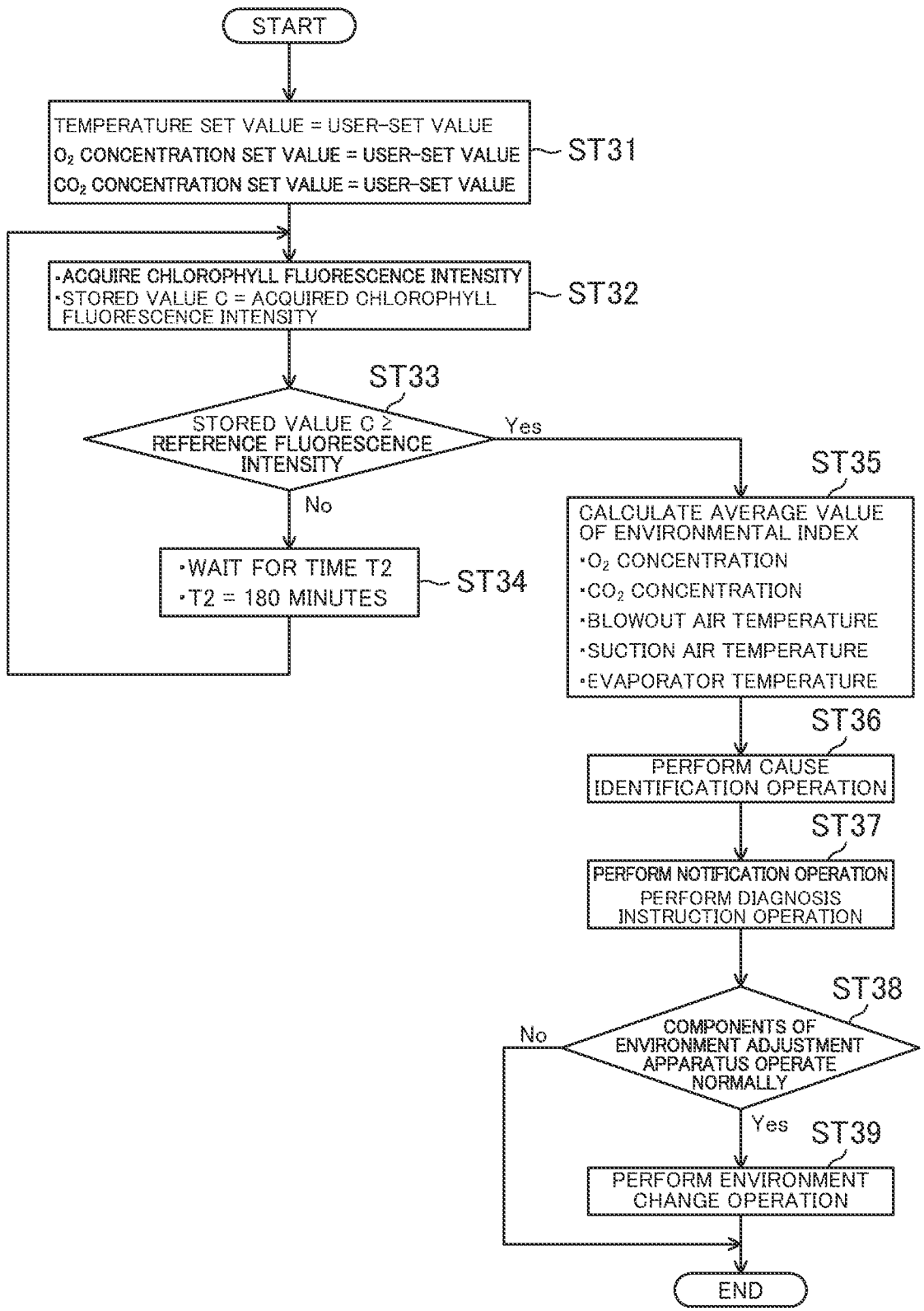
FIG. 6 is a flowchart illustrating a main operation performed by the quality determination unit of the controller according to the first embodiment.

In the processing from Steps ST66 to ST70, the quality determination unit (64) of the present embodiment performs the same processing as the processing from Steps ST35 to ST39 shown in FIG. 6. Specifically, the processing of Step ST66 is the same as the processing of Step ST35 in FIG. 6, the processing of Step ST67 is the same as the processing of Step ST36 in FIG. 6, the processing of Step ST68 is the same as the processing of Step ST37 in FIG. 6, the processing of Step ST69 is the same as the processing of Step ST38 in FIG. 6, and the processing of Step ST70 is the same as the processing of Step ST39 in FIG. 6. When the processing of Step ST70 ends, the quality determination unit (64) ends the main operation.

Fourth Embodiment

Figure 9:
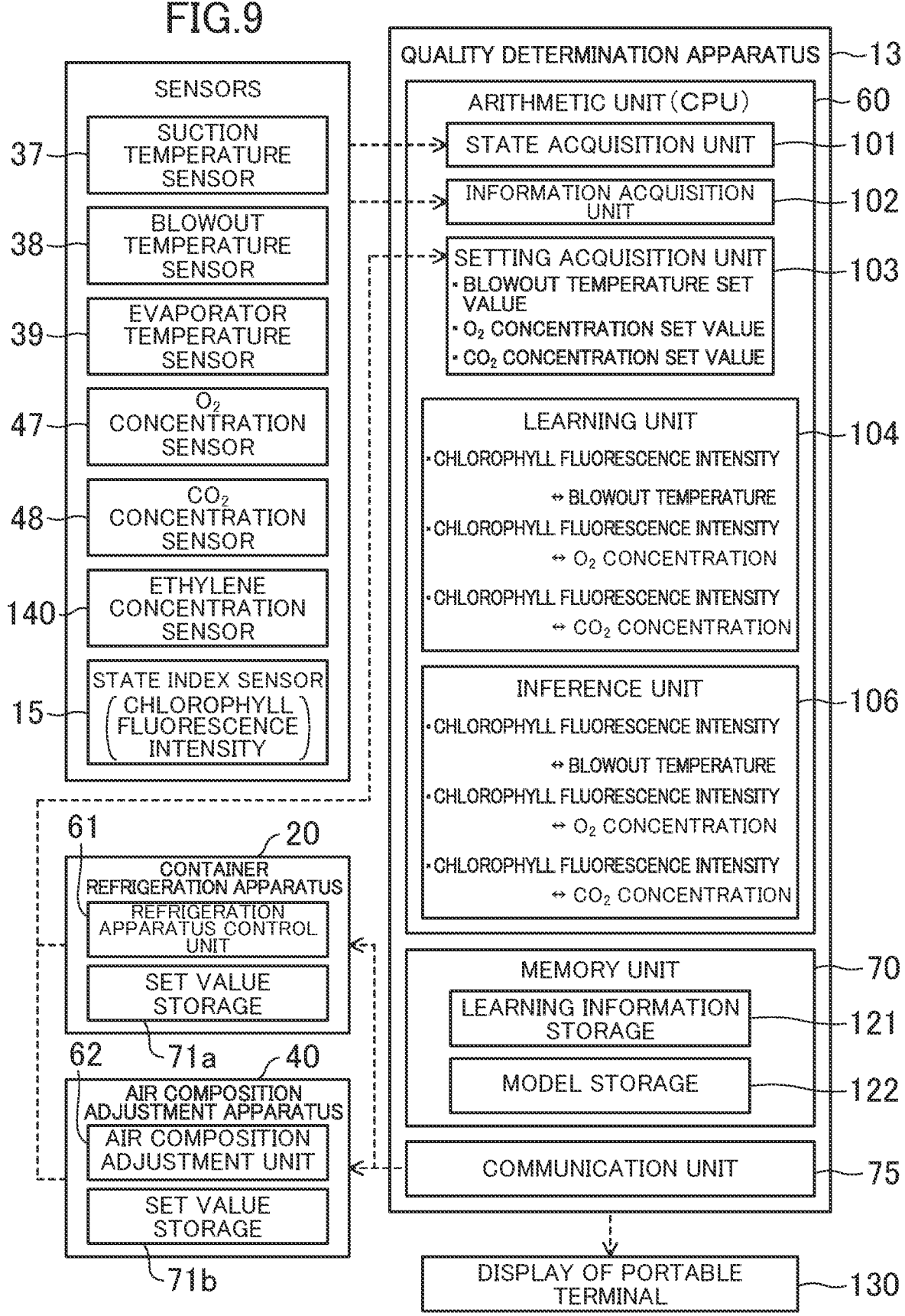
FIG. 9 is a block diagram illustrating a configuration of a quality determination apparatus according to a fourth embodiment and a relationship between a container refrigeration apparatus, an air composition adjustment apparatus, sensors, and the quality determination apparatus.

A fourth embodiment will be described below. A quality determination apparatus (13) of the present embodiment is a portable terminal (e.g., a smartphone) in which a quality determination program is installed, As illustrated in FIG. 9, a quality determination apparatus (13) of the present embodiment includes an arithmetic unit (60), a memory unit (70), and a communication unit (75). The quality determination apparatus (13) of the present embodiment executes a quality determination method for a shipping container (1) provided with the container refrigeration apparatus (20), air composition adjustment apparatus (40), and state index sensors (15) of the first embodiment.

—Refrigeration Apparatus Control Unit, Air Composition Adjustment Unit, Set Value Storage—

The container refrigeration apparatus (20) of the present embodiment is provided with a refrigeration apparatus control unit (61) and a set value storage (71a). The set value storage (71a) stores a blowout temperature set value, just like the set value storage (71) of the first embodiment. As in the first embodiment, the refrigeration apparatus control unit (61) controls the operation of the container refrigeration apparatus (20) so that the measurement of the blowout temperature sensor (38) reaches the blowout temperature set value.

In the present embodiment, the air composition adjustment apparatus (40) is provided with an air composition adjustment unit (62) and a set value storage (71b). The set value storage (71b) stores an oxygen concentration set value and a carbon dioxide concentration set value, just like the set value storage (71) of the first embodiment. As in the first embodiment, the air composition adjustment unit (62) controls the operation of the air composition adjustment apparatus (40) so that the measurement of the oxygen concentration sensor (47) reaches the oxygen concentration set value, and the measurement of the carbon dioxide concentration sensor (48) reaches the carbon dioxide concentration set value.

—Arithmetic Unit—

As illustrated in FIG. 9, the controller (50) includes an arithmetic unit (60), a memory unit (70), and a communication unit (75).

The arithmetic unit (60) is comprised of a microprocessor provided in the portable terminal. The arithmetic unit (60) functions as a state acquisition unit (101), an information acquisition unit (102), a setting acquisition unit (103), a learning unit (104), and an inference unit (106) when executing the quality determination program stored in the memory unit (70).

Further, the arithmetic unit (60) performs an operation of transmitting "an instruction to display predetermined information" to a display (130) of the portable terminal constituting the quality determination apparatus (13). In the present embodiment, the display (130) of the portable terminal constitutes a notification device for notifying a human of information.

<State Acquisition Unit>

The state acquisition unit (101) executes first acquisition processing. The first acquisition processing is acquisition of a state index indicating the state of the target articles (7) contained in the cargo space (5). The first acquisition processing is a first processing step of the quality determination method.

Specifically, the state acquisition unit (101) acquires the measurements of the chlorophyll fluorescence intensity outputted by the state index sensors (15) via the communication unit (75). The state acquisition unit (101) acquires the measurements of the three state index sensors (15) and calculates an arithmetic mean of the acquired three measurements. Then, the state acquisition unit (101) outputs the arithmetic mean of the three measurements in association with time at which the measurements were acquired from the state index sensors (15).

<Information Acquisition Unit>

The information acquisition unit (102) executes second acquisition processing. The second acquisition processing is acquisition of environmental information about the internal environment of the cargo space (5). The second acquisition processing is a second processing step of the quality determination method.

Specifically, the information acquisition unit (102) acquires, via the communication unit (75), a suction temperature measurement outputted by the suction temperature sensor (37), a blowout temperature measurement outputted by the blowout temperature sensor (38), an evaporator temperature measurement outputted by the evaporator temperature sensor (39), an oxygen concentration measurement outputted by the oxygen concentration sensor (47), a carbon dioxide concentration measurement outputted by the carbon dioxide concentration sensor (48), and an ethylene concentration measurement outputted by the ethylene concentration sensor (140). The information acquisition unit (102) outputs the measurements acquired from the sensors (37, 38, 39, 47, 48, 140) in association with times at which the measurements were acquired from the sensors (37, 38, 39, 47, 48, 140).

Note that the suction temperature measured by the suction temperature sensor (37), the blowout temperature measured by the blowout temperature sensor (38), and the evaporator temperature measured by the evaporator temperature sensor (39) are physical quantities indicating the operating state of the container refrigeration apparatus (20) and correlating with the temperature of the cargo space (5).

<Setting Acquisition Unit>

The setting acquisition unit (103) executes third acquisition processing. The third acquisition processing is acquisition of setting information that is a set value of the "environmental index indicating the internal environment of the cargo space (5)." The third acquisition processing is a third processing step of the quality determination method.

Specifically, the setting acquisition unit (103) acquires, via the communication unit (75), the blowout temperature set value stored in the set value storage (71*a*) of the container refrigeration apparatus (20). The setting acquisition unit (103) acquires the oxygen concentration set value and the carbon dioxide concentration set value stored in the set value storage (71*b*) of the air composition adjustment apparatus (40) via the communication unit (75). The setting acquisition unit (103) outputs the acquired blowout temperature set value, oxygen concentration set value, and carbon dioxide concentration set value in association with times at which these set values were acquired.

<Learning Unit>

The learning unit (104) performs so-called machine learning. The learning unit (104) executes learning processing. The learning processing is generation of state estimation models (111 to 113). The learning processing is a learning step of the quality determination method.

The state estimation models (111 to 113) are models that have learned a correlation between the state index acquired by the state acquisition unit (101), the environmental information acquired by the information acquisition unit (102), and the setting information acquired by the setting acquisition unit (103). Examples of the state estimation models (111 to 113) include a neural network (NN) model, a random forest model, and a support vector machine (SVM) model.

The learning unit (104) generates a first state estimation model (111) related to the chlorophyll fluorescence intensity and the blowout temperature set value, a second state estimation model (112) related to the chlorophyll fluorescence intensity and the oxygen concentration set value, and a third state estimation model (113) related to the chlorophyll fluorescence intensity and the carbon dioxide concentration set value. Details of the learning processing executed by the learning unit (104) will be described later.

<Inference Unit>

The inference unit (106) executes determination processing. The determination processing is calculating an "estimated value of a state index (chlorophyll fluorescence intensity in the present embodiment)" by inputting the environmental information acquired by the information acquisition unit (102) and the setting information acquired by the setting acquisition unit (103) to the state estimation models (111 to 113), and determining whether a "sign condition indicating a sign of degradation of the target articles (7)" is met based on the calculated "estimated value of the state index." The determination processing is a determination step of the quality determination method. Details of the determination processing will be described later.

The inference unit (106) also executes environment change processing. The environment change processing is instructing the container refrigeration apparatus (20) and the air composition adjustment apparatus (40) constituting the environment adjustment apparatus (14) to change the internal environment of the cargo space (5) in order to keep the target articles (7) from degradation when a determination is made that the sign condition is met in the determination processing. The environment change processing is an environment change step of the quality determination method. Details of the environment change processing will be described later.

—Memory Unit—

As in the first embodiment, the memory unit (70) is, for example, a semiconductor memory comprised of an integrated circuit. The memory unit (70) stores a quality determination program and data necessary for the operation of the quality determination apparatus (13).

<Learning Information Storage>

As illustrated in FIG. 9, the memory unit (70) functions as a learning information storage (121) and a model storage (122).

The learning information storage (121) stores learning information used by the learning unit (104) when executing the processing. Specifically, the learning information storage (121) stores, as the learning information, data that associates "the measurement (chlorophyll fluorescence intensity in the present embodiment) of the state index sensor (15) acquired as the state index by the state acquisition unit (101)" with "time when the state acquisition unit (101) acquired the measurement."

The learning information storage (121) also stores, as the learning information, data that associates "the measurements of the sensors (37, 38, 39, 47, 48, 140) acquired as the environmental information by the information acquisition unit (102)" and "times when the information acquisition unit (102) acquired the measurements."

The learning information storage (121) further stores, as the learning information, data that associates "the blowout temperature set value, the oxygen concentration set value, and the carbon dioxide concentration set value acquired as the setting information by the setting acquisition unit (103)" with "times when the setting acquisition unit (103) acquired the set values."

<Model Storage>

The model storage (122) stores the three state estimation models (111 to 113) generated by the learning unit (104). The model storage (122) stores various parameters constituting the state estimation models (111 to 113).

—Communication Unit—

The communication unit (75) is configured to wirelessly communicate with the container refrigeration apparatus (20), the air composition adjustment apparatus (40), and the state index sensors (15).

—Learning Processing—

The learning processing performed by the learning unit (104) will be described below. The learning processing is a learning phase of machine learning. The learning processing according to the present embodiment is generating the first state estimation model (111) related to the blowout temperature set value, the second state estimation model (112) related to the oxygen concentration set value, and the third state estimation model (113) related to the carbon dioxide concentration set value.

Figure 10:
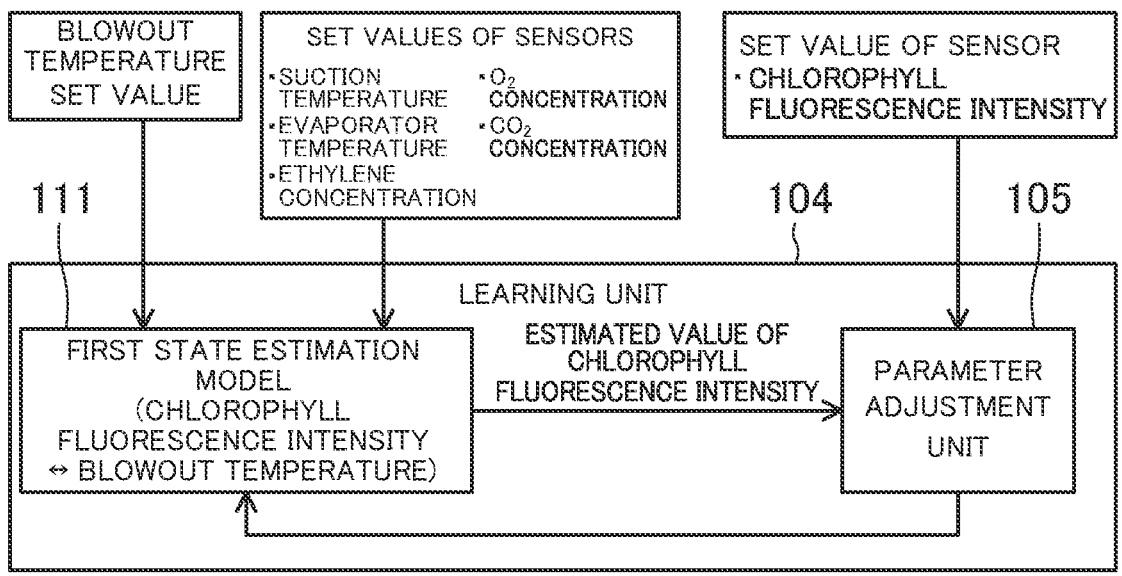
FIG. 10 is a block diagram illustrating a configuration and function of a learning unit of the quality determination apparatus according to the fourth embodiment related to a blowout temperature.
Figure 12:
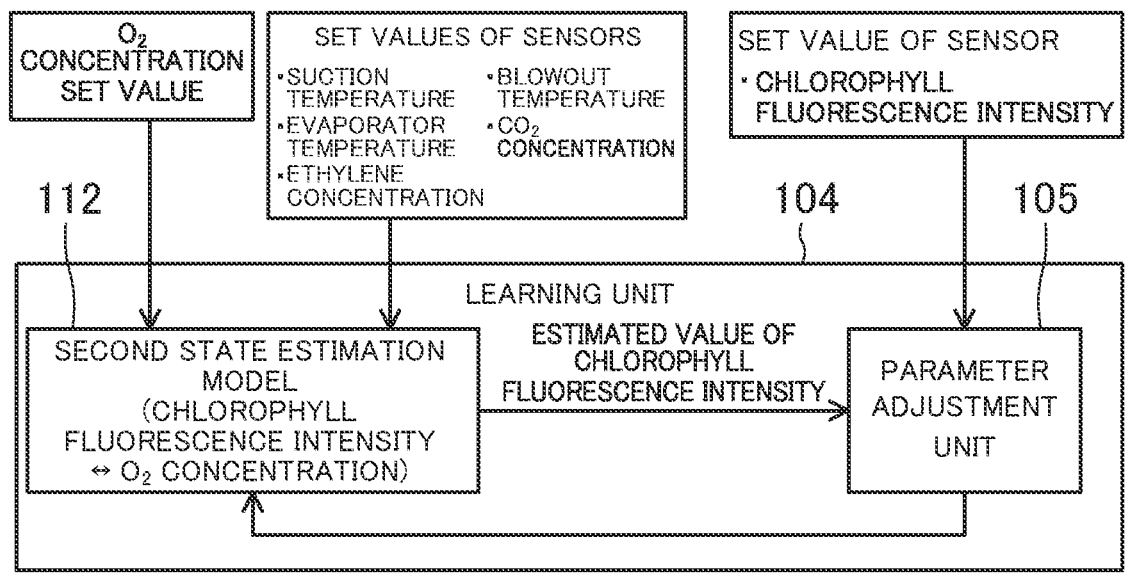
FIG. 12 is a block diagram illustrating a configuration and function of the learning unit of the quality determination apparatus according to the fourth embodiment related to an oxygen concentration.
Figure 14:
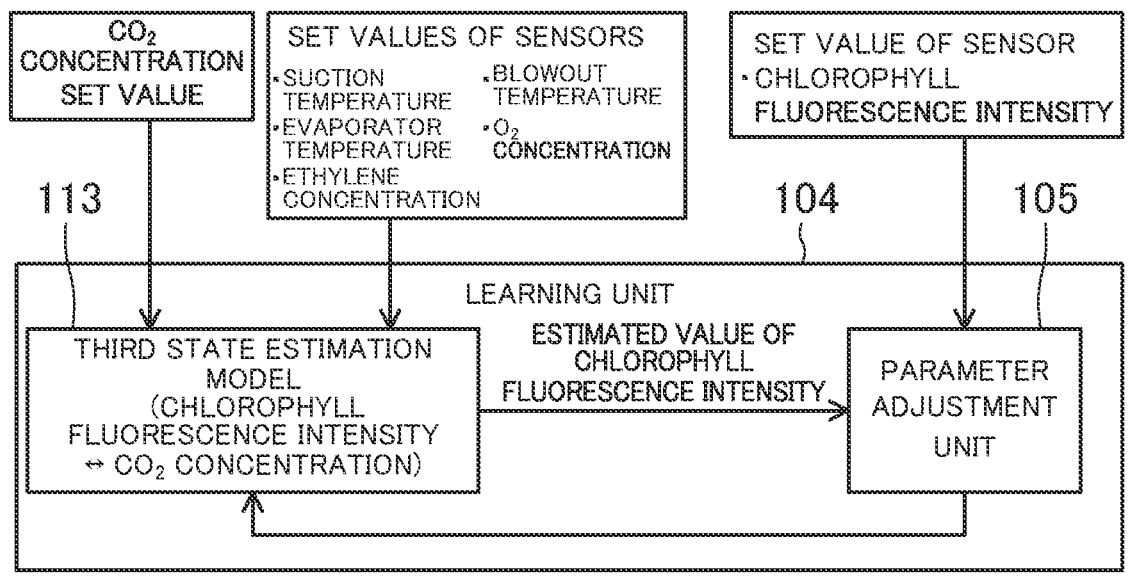
FIG. 14 is a block diagram illustrating a configuration and function of the learning unit of the quality determination apparatus according to the fourth embodiment related to a carbon dioxide concentration.

As illustrated in FIGS. 10, 12, and 14, the learning unit (104) includes a parameter adjustment unit (105). The parameter adjustment unit (105) performs processing to adjust various parameters constituting the state estimation models (111 to 113).

In the learning processing described below, the learning unit (104) first reads the learning information from the learning information storage (121).

<First State Estimation Model Related to Blowout Temperature Set Value>

Processing that the learning unit (104) executes to generate the "first state estimation model (111) related to the blowout temperature set value" will be described with reference to FIG. 10.

The learning unit (104) inputs a predetermined data set to the first state estimation model (111). The data set inputted to the first state estimation model (111) by the learning unit (104) includes "measurements of the suction temperature, the evaporator temperature, the ethylene concentration, the oxygen concentration, and the carbon dioxide concentration" which were acquired at substantially the same time and "the blowout temperature set value." The learning unit (104) inputs this data set to the first state estimation model (111) to calculate an estimated value of the chlorophyll fluorescence intensity. The calculated estimated value of the chlorophyll fluorescence intensity is inputted to the parameter adjustment unit (105).

The learning unit (104) inputs the "measurement of chlorophyll fluorescence intensity" acquired at substantially the same time as the data set inputted to the first state estimation model (111) to the parameter adjustment unit (105). The parameter adjustment unit (105) compares the "estimated value of chlorophyll fluorescence intensity calculated using the first state estimation model (111)" with the "measurement of chlorophyll fluorescence intensity." Then, the parameter adjustment unit (105) adjusts various parameters constituting the first state estimation model (111) to reduce the difference between the "estimated value of chlorophyll fluorescence intensity" and the "measurement of chlorophyll fluorescence intensity."

The learning unit (104) repeats the processing to adjust the parameters constituting the first state estimation model (111) using a plurality of data sets corresponding to different times and the "measurement of chlorophyll fluorescence intensity" corresponding to each data sett. As a result, the first state estimation model (111) that has learned is generated.

<Second State Estimation Model Related to Oxygen Concentration Set Value>

Processing that the learning unit (104) executes to generate the "second state estimation model (112) related to the oxygen concentration set value" will be described with reference to FIG. 12.

The learning unit (104) inputs a predetermined data set to the second state estimation model (112). The data set inputted to the second state estimation model (112) by the learning unit (104) includes "measurements of the suction temperature, the blowout temperature, the evaporator temperature, the ethylene concentration, and the carbon dioxide concentration" which were acquired at substantially the same time and "the oxygen concentration set value." The learning unit (104) inputs this data set to the second state estimation model (112) to calculate an estimated value of the chlorophyll fluorescence intensity. The calculated estimated value of the chlorophyll fluorescence intensity is inputted to the parameter adjustment unit (105).

The learning unit (104) inputs the "measurement of chlorophyll fluorescence intensity" acquired at substantially the same time as the data set inputted to the second state estimation model (112) to the parameter adjustment unit (105). The parameter adjustment unit (105) compares the "estimated value of chlorophyll fluorescence intensity calculated using the second state estimation model (112)" with the "measurement of chlorophyll fluorescence intensity." Then, the parameter adjustment unit (105) adjusts various parameters constituting the second state estimation model (112) to reduce the difference between the "estimated value of chlorophyll fluorescence intensity" and the "measurement of chlorophyll fluorescence intensity."

The learning unit (104) repeats the processing to adjust the parameters constituting the second state estimation model (112) using a plurality of data sets corresponding to different times and the "measurement of chlorophyll fluorescence intensity" corresponding to each data set. As a result, the second state estimation model (112) that has learned is generated.

<Third State Estimation Model Related to Carbon Dioxide Concentration Set Value>

Processing that the learning unit (104) executes to generate the "third state estimation model (113) related to the carbon dioxide concentration se value" will be described with reference to FIG. 14.

The learning unit (104) inputs a predetermined data set to the third state estimation model (113). The data set inputted to the third state estimation model (113) by the learning unit (104) includes "measurements of the suction temperature, the blowout temperature, the evaporator temperature, the ethylene concentration, and the oxygen concentration" which were acquired at substantially the same time and "the carbon dioxide concentration set value." The learning unit (104) inputs this data set to the third state estimation model (113) to calculate an estimated value of the chlorophyll fluorescence intensity. The calculated estimated value of the chlorophyll fluorescence intensity is inputted to the parameter adjustment unit (105).

The learning unit (104) inputs the "measurement of chlorophyll fluorescence intensity" acquired at substantially the same time as the data se inputted to the third state estimation model (113) to the parameter adjustment unit (105). The parameter adjustment unit (105) compares the "estimated value of chlorophyll fluorescence intensity calculated using the third state estimation model (113)" with the "measurement of chlorophyll fluorescence intensity." Then, the parameter adjustment unit (105) adjusts various parameters constituting the third state estimation model (113) to reduce the difference between the "estimated value of chlorophyll fluorescence intensity" and the "measurement of chlorophyll fluorescence intensity."

The learning unit (104) repeats the processing to adjust the parameters constituting the third state estimation model (113) using a plurality of data sets corresponding to different times and the "measurement of chlorophyll fluorescence intensity" corresponding to each data set. As a result, the third state estimation model (113) that has learned is generated.

—Environment Change Processing—

Figure 11:
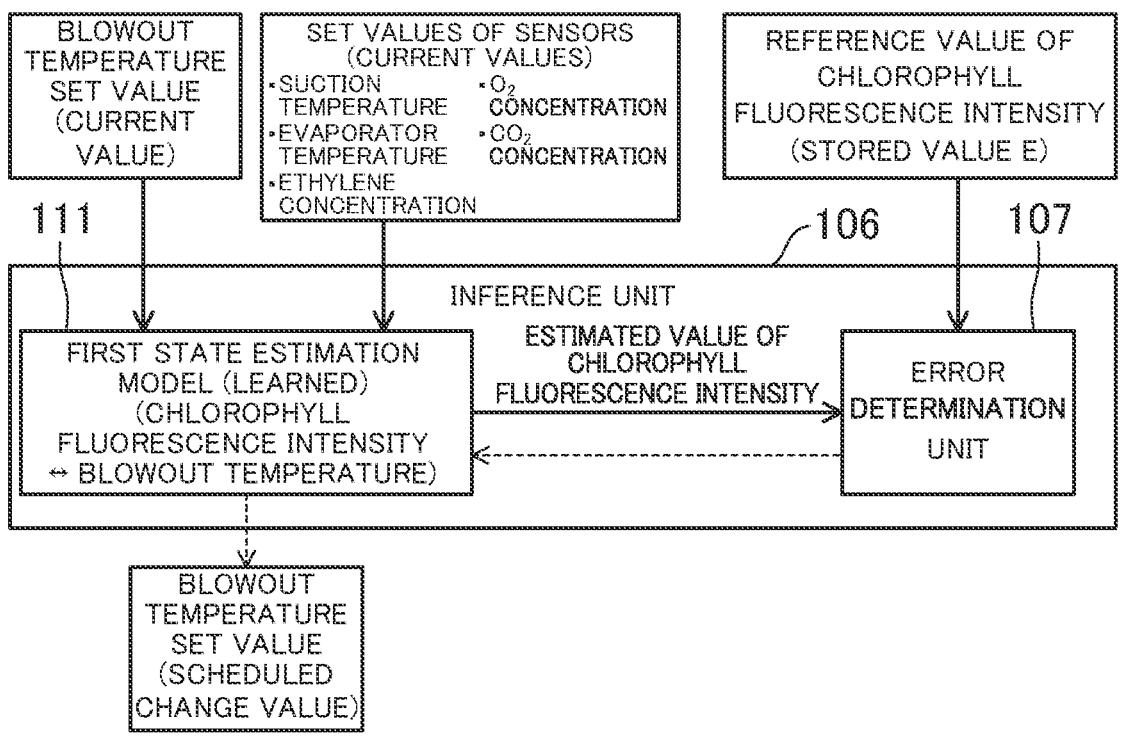
FIG. 11 is a block diagram illustrating a configuration and function of an inference unit of the quality determination apparatus according to the fourth embodiment related to a blowout temperature.
Figure 13:
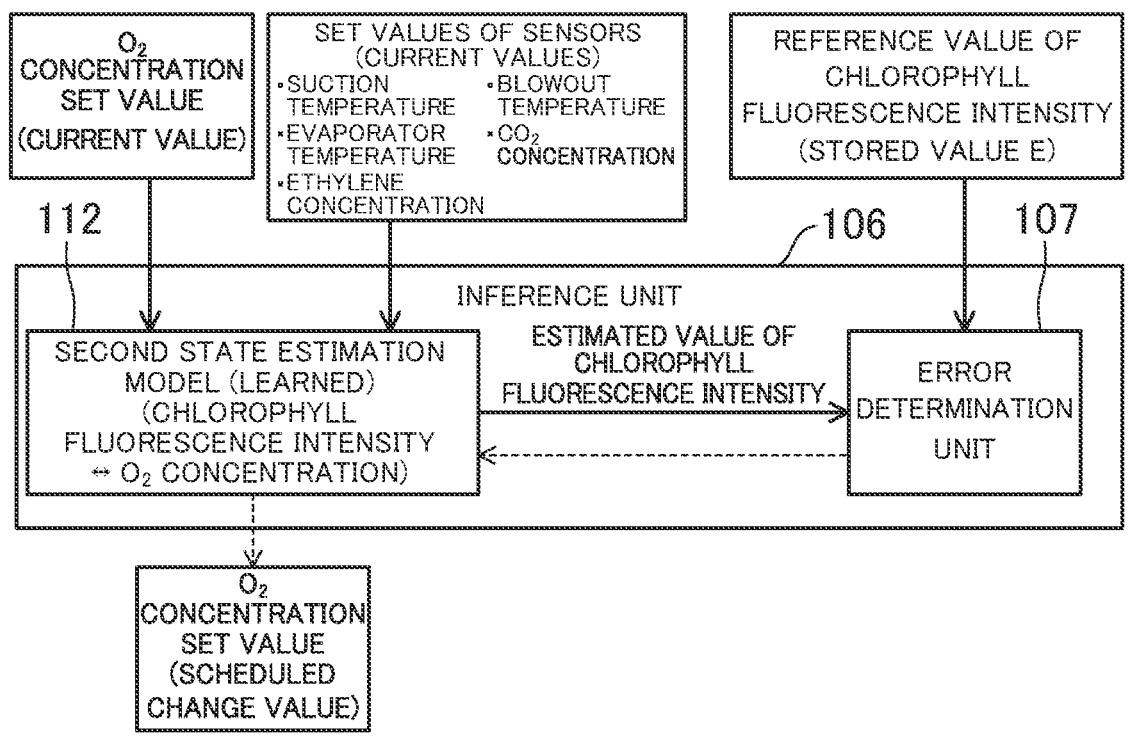
FIG. 13 is a block diagram illustrating a configuration and function of the inference unit of the quality determination apparatus according to the fourth embodiment related to an oxygen concentration.
Figure 15:
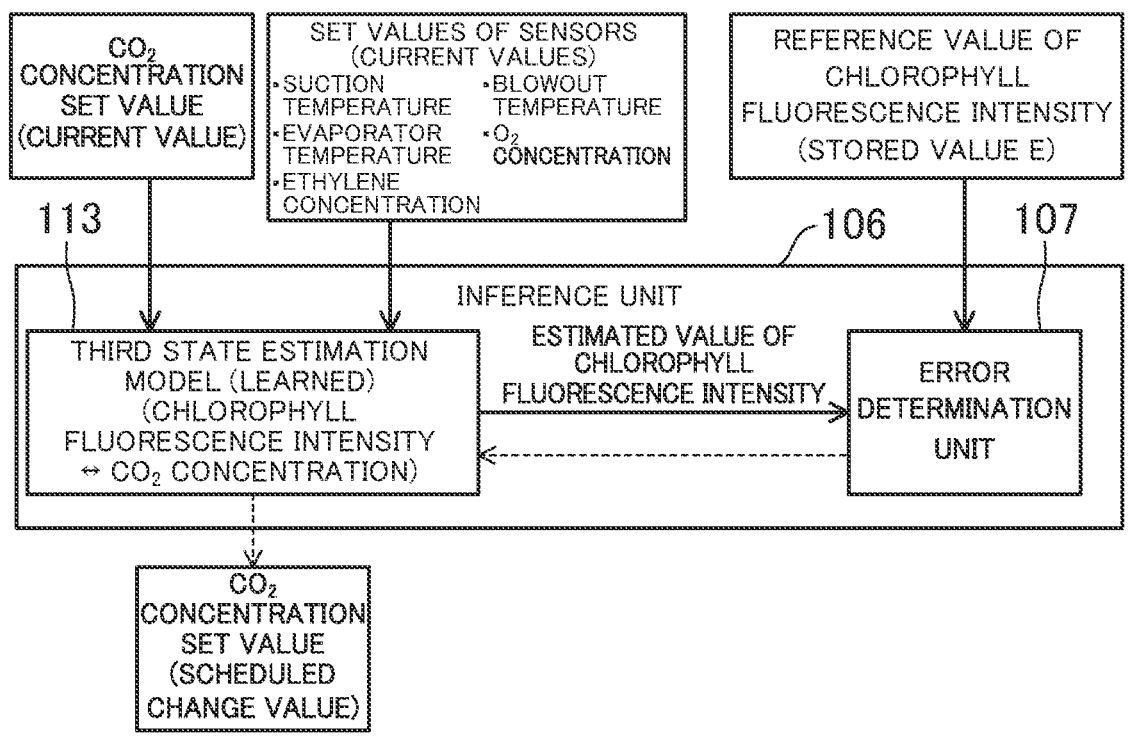
FIG. 15 is a block diagram illustrating a configuration and function of the inference unit of the quality determination apparatus according to the fourth embodiment related to a carbon dioxide concentration.

The environment change processing executed by the inference unit (106) will be described below. The environment change processing is an inference phase of machine learning. The environment change processing according to the present embodiment is calculation of scheduled change values of the blowout temperature set value, the oxygen concentration set value, and the carbon dioxide concentration set value. As illustrated in FIGS. 11, 13, and 15, the inference unit (106) includes an error determination unit (107).

The inference unit (106) acquires the environmental information outputted by the information acquisition unit (102) at a point of time and the setting information outputted by the setting acquisition unit (103) at that point of time. The inference unit (106) reads the learned state estimation models (111 to 113) from the model storage (122) of the memory unit (70). Further, the inference unit (106) reads a "reference value of chlorophyll fluorescence intensity" from the memory unit (70). The "reference value of chlorophyll fluorescence intensity" is a measurement of the chlorophyll fluorescence intensity outputted by the state index sensor (15) when the target articles (7) are not presumed to be degraded.

<Scheduled Change Value of Blowout Temperature Set Value>

Processing executed by the inference unit (106) to calculate the "scheduled change value of the suction temperature set value" will be described with reference to FIG. 11.

The inference unit (106) inputs a predetermined data set to the learned first state estimation model (111). The data set inputted to the first state estimation model (111) by the inference unit (106) includes the blowout temperature set value outputted as the setting information by the setting acquisition unit (103), and the measurements of the suction temperature, the evaporator temperature, the ethylene concentration, the oxygen concentration, and the carbon dioxide concentration acquired as the environmental information by the information acquisition unit (102). The inference unit (106) inputs this data set to the learned first state estimation model (111) to calculate an estimated value of the chlorophyll fluorescence intensity. The calculated estimated value of the chlorophyll fluorescence intensity is inputted to the error determination unit (107).

The "reference value of chlorophyll fluorescence intensity" is inputted to the error determination unit (107). The error determination unit (107) calculates a difference between the "estimated value of chlorophyll fluorescence intensity" calculated using the learned first state estimation model (111) and "the reference value of chlorophyll fluorescence intensity," i.e., an error value.

The inference unit (106) performs processing based on a back propagation method using the first state estimation model (111) and the error value calculated by the error determination unit (107), thereby calculating. the blowout temperature set value that makes the error value approach zero. The inference unit (106) outputs the calculated blowout temperature set value as a "scheduled change value of the blowout temperature set value." The "scheduled change value of the blowout temperature set value" is a blowout temperature set value adjusted to keep the target articles (7) from degradation.

<Scheduled Change Value of Oxygen Concentration Set Value>

Processing executed by the inference unit (106) to calculate the "scheduled change value of the oxygen concentration set value" will be described with reference to FIG. 13.

The inference unit (106) inputs a predetermined data set to the learned second state estimation model (112). The data set inputted to the second state estimation model (112) by the inference unit (106) includes the oxygen concentration set value outputted as the setting information by the setting acquisition unit (103), and the measurements of the suction temperature, the blowout temperature, the evaporator temperature, the ethylene concentration, and the carbon dioxide concentration acquired as the environmental information by the information acquisition unit (102). The inference unit (106) inputs this data set to the learned second state estimation model (112) to calculate an estimated value of the chlorophyll fluorescence intensity. The calculated estimated value of the chlorophyll fluorescence intensity is inputted to the error determination unit (107).

The "reference value of chlorophyll fluorescence intensity" is inputted to the error determination unit (107). The error determination unit (107) calculates a difference between the "estimated value of chlorophyll fluorescence intensity" calculated using the learned second state estimation model (112) and "the reference value of chlorophyll fluorescence intensity," i.e., an error value.

The inference unit (106) executes processing based on the back propagation method using the second state estimation model (112) and the error value calculated by the error determination unit (107), thereby calculating the oxygen concentration set value that makes the error value approach zero. The inference unit (106) outputs the calculated oxygen concentration set value as a "scheduled change value of the oxygen concentration set value." The "scheduled change value of the oxygen concentration set value" is an oxygen concentration set value adjusted to keep the target articles (7) from degradation.

<Scheduled Change Value of Carbon Dioxide Concentration Set Value>

Processing executed by the inference unit (106) to calculate the "scheduled change value of the carbon dioxide concentration set value" will be described with reference to FIG. 15.

The inference unit (106) inputs a predetermined data set to the learned third state estimation model (113). The data set inputted to the third state estimation model (113) by the inference unit (106) includes the carbon dioxide concentration set value outputted as the selling information by the setting acquisition unit (103), and the measurements of the suction temperature, the blowout temperature, the evaporator temperature, the ethylene concentration, and the oxygen concentration acquired as the environmental information by the information acquisition unit (102). The inference unit (106) inputs this data set to the learned third state estimation model (113) to calculate an estimated value of the chlorophyll fluorescence intensity. The calculated estimated value of the chlorophyll fluorescence intensity is inputted to the error determination unit (107).

The "reference value of chlorophyll fluorescence intensity" is inputted to the error determination unit (107). The error determination unit (107) calculates a difference between the "estimated value of chlorophyll fluorescence intensity" calculated using the learned third state estimation model (113) and "the reference value of chlorophyll fluorescence intensity."

The inference unit (106) executes processing based on the back propagation method using the third state estimation model (113) and the error value calculated by the error determination unit (107), thereby calculating the carbon dioxide concentration set value that makes the error value approach zero. The inference unit (106) outputs the calculated carbon dioxide concentration set value as a "scheduled change value of the carbon dioxide concentration set value." The "scheduled change value of the carbon dioxide concentration set value" is a carbon dioxide concentration set value adjusted to keep the target articles (7) from degradation.

—Processing Executed by Quality Determination Apparatus—

Figure 16:
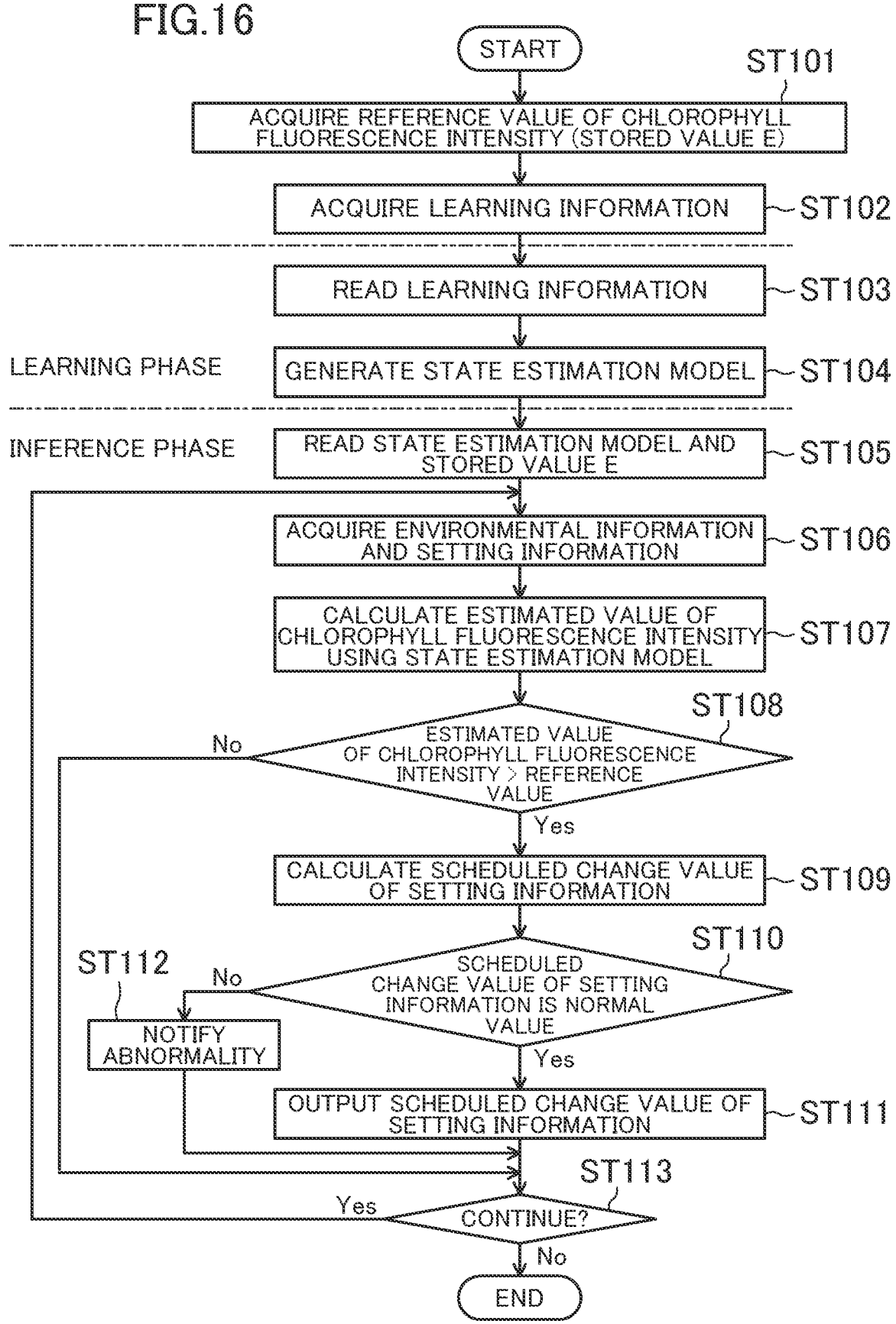
FIG. 16 is a flowchart illustrating processing performed by the quality determination apparatus according to the fourth embodiment.

Processing executed by the quality determination apparatus (13) will be described with reference to the flowchart of FIG. 16.

When pre-trip inspection (PTI) of the container refrigeration apparatus (20) and the air composition adjustment apparatus (40) is completed, the container refrigeration apparatus (20) is operated first to lower the temperature of the cargo space (5), acid then the target articles (7) are carried into the cargo space (5).

When a stable temperature condition indicating that the temperature of the cargo space is stable is met, the quality determination apparatus (13) executes the processing of Step ST101. The stable temperature condition is, for example, a condition that "the measurement of the blowout temperature sensor (38) is kept within a range of the blowout temperature set value±1° C. fix a predetermined time (e.g., 60 minutes)."

(Step ST101)

In the processing of Step ST101, the state acquisition unit (101) of the quality determination apparatus (13) acquires the measurements of the state index sensors (15). The state acquisition unit (101) acquires the measurements of chlorophyll fluorescence intensity of the three state index sensors (15) and calculates an arithmetic mean of the acquired three measurements. The state acquisition unit (101) stores the calculated arithmetic mean of the measurements as a stored value E in the memory unit (70).

At a point of time when the processing of Step ST101 is performed, the composition of the air in the cargo space (5) is substantially the same as the composition of the air outside the cargo space (5) (i.e., the atmospheric air). The processing of Step ST101 is performed at a point of time when not much time has passed since the target articles (7) were carried into the cargo space (5). Thus, the target articles (7) in the cargo space (5) are not substantially degraded at the point of time when the processing of Step ST101 is performed.

The stored value E stored in the memory unit (70) by the state acquisition unit (101) in the processing of Step ST101 is the chlorophyll fluorescence intensity measured by the state index sensor (15) when the target articles (7) are not presumed to be degraded. That is, the stored value E is a "reference value of chlorophyll fluorescence intensity."

After the processing of Step ST101 ends, the air composition adjustment apparatus (40) is activated to lower the oxygen concentration of the air in the cargo space (5).

The processing of Step ST101 may be performed after the air composition adjustment apparatus (40) is activated. In this case, the processing of Step ST101 is performed when the measurements of the oxygen concentration sensor (47) and the carbon dioxide sensor (48) are substantially constant.

(Step ST102)

When the air composition adjustment apparatus (40) is activated after the end of the processing of Step ST101 and the measurements of the oxygen concentration sensor (47) and the carbon dioxide concentration sensor (48) are stabilized to some extent, the quality determination apparatus (13) executes the processing of Step ST102.

In the processing of Step ST102, the quality determination apparatus (13) stores the state index acquired by the state acquisition unit (101), the environmental information acquired by the information acquisition unit (102), and the set value acquired by the setting acquisition unit (103) as the learning information in the learning information storage (121) of the memory unit (70).

(Step ST103)

In the processing of the subsequent Step ST103, the learning unit (104) of the quality determination apparatus (13) reads the learning information from the learning information storage (121).

(Step ST104)

In the processing of the subsequent Step ST104, the learning unit (104) of the quality determination apparatus (13) executes learning processing. Specifically, the learning unit (104) executes processing to generate the first state estimation model (111) related to the suction temperature set value, processing to generate the second state estimation model (112) related to the oxygen concentration set value, and processing to generate the third state estimation model (113) related to the carbon dioxide concentration set value. Details of the processing are as described above. The learning unit (104) stores the learned state estimation models (111 to 113) in the model storage (122) of the memory unit (70).

(Step ST105)

In the processing of the subsequent Step ST105, the inference unit (106) of the quality determination apparatus (13) reads the learned state estimation models (111 to 113) and the reference value (stored value E) of the chlorophyll fluorescence intensity stored in the memory unit (70) in the processing of Step ST101.

(Step ST106)

In the processing of the subsequent Step ST106, the information acquisition unit (102) of the quality determination apparatus (13) acquires the environmental information, and the setting acquisition unit (103) acquires the setting information.

(Step ST107)

In the processing of the subsequent Step ST107, the inference unit (106) of the quality determination apparatus (13) calculates an estimated value of chlorophyll fluorescence intensity using the state estimation models (111 to 113). Specifically, the inference unit (106) inputs a predetermined data set to each of the first state estimation model (111), the second state estimation model (112), and the third state estimation model (113), and calculates the estimated value of chlorophyll fluorescence intensity. Details of the processing to calculate the estimated value of chlorophyll fluorescence intensity using the state estimation models (111 to 113) are as described above.

(Step ST108)

In the processing of the subsequent Step ST108, the arithmetic unit (60) of the quality determination apparatus (13) executes determination processing. The determination processing is determining whether the "sign condition indicating the sign of degradation of the target articles (7)" is met based on the "estimated value of chlorophyll fluorescence intensity" calculated in Step ST107. This determination processing is a determination step of the quality determination method.

The sign condition is a condition that the "estimated value of chlorophyll fluorescence intensity" calculated in Step ST107 exceeds the "reference value of chlorophyll fluorescence intensity (stored value E)." In the processing of Step ST108, the arithmetic unit (60) compares each of the "estimated value of chlorophyll fluorescence intensity" calculated based on the first state estimation model (111), the "estimated value of chlorophyll fluorescence intensity" calculated based on the second state estimation model (112), and the "estimated value of chlorophyll fluorescence intensity" calculated based on the third state estimation model (113) with the "reference value of chlorophyll fluorescence intensity." Then, the arithmetic unit (60) determines that the sign condition is met when at least one of the three "estimated values of chlorophyll fluorescence intensity" exceeds the "reference value of chlorophyll fluorescence intensity."

When a determination is made that the sign condition is met, the quality determination apparatus (13) then executes the processing of Step ST109. When a determination is made that the sign condition is not met, the quality determination apparatus (13) then executes the processing of Step ST113.

(Step ST109)

In the processing of Step ST109, the inference unit (106) performs processing to calculate the scheduled change values of the blowout temperature set value, the oxygen concentration set value, and the carbon dioxide concentration set value. Details of the processing to calculate the scheduled change values of these set values are as described above. The inference unit (106) stores the calculated scheduled change values of the set values in the memory unit (70).

(Step ST110)

In the processing of the subsequent Step ST110, the inference unit (106) determines whether the scheduled change values of the blowout temperature set value, the oxygen concentration set value, and the carbon dioxide concentration set value calculated in Step ST109 are normal values.

When the scheduled change value of the blowout temperature set value is within a normal range of the blowout temperature, the inference unit (106) determines that the scheduled change value of the blowout temperature set value is a normal value. When the scheduled change value of the oxygen concentration set value is within a normal range of the oxygen concentration, the inference unit (106) determines that the scheduled change value of the oxygen concentration set value is a normal value. When the scheduled change value of the carbon dioxide concentration set value is within a normal range of the carbon dioxide concentration, the inference unit (106) determines that the scheduled change value of the carbon dioxide concentration set value is a normal value.

The normal range of each of the suction temperature, the oxygen concentration, and the carbon dioxide concentration may be a numerical value range that can be set for each of the suction temperature, the oxygen concentration, and the carbon dioxide concentration, or may be a numerical value range that is arbitrarily set for each of the suction temperature, the oxygen concentration, and the carbon dioxide concentration by an operator.

When all the scheduled change values of the blowout temperature set value, the oxygen concentration set value, and the carbon dioxide concentration set value are the normal values, the inference unit (106) of the arithmetic unit (60) executes the processing of Step ST111. When at least one of the scheduled change values of the blowout temperature set value, the oxygen concentration set value, and the carbon dioxide concentration set value is not the normal value, the arithmetic unit (60) performs the processing of Step ST112.

(Step ST111)

In the processing of Step ST111, the inference unit (106) transmits the "scheduled change value of the suction temperature set value" calculated in Step ST109 to the container refrigeration apparatus (20). The container refrigeration apparatus (20) adjusts the temperature of the air in the cargo space (5) using the received "scheduled change value of the suction temperature set value."

In the processing of Step ST111, the inference unit (106) transmits the "scheduled change value of the oxygen concentration set value" and the scheduled change value of the carbon dioxide concentration set value" calculated in Step ST109 to the air composition adjustment apparatus (40). The air composition adjustment apparatus (40) adjusts the oxygen concentration of the air in the cargo space (5) using the received the "scheduled change value of the oxygen concentration set value," and adjusts the carbon dioxide concentration of the air in the cargo space (5) using the received the "scheduled change value of the carbon dioxide concentration set value."

A series of the processing from Steps ST109 to ST111 performed by the inference unit (106) is the environment change processing.

(Step ST112)

In the processing of Step ST112, the arithmetic unit (60) performs processing to notify the operator that the scheduled change value of the set value is an abnormal value deviating from the normal value. Specifically, the arithmetic unit (60) transmits an instruction for displaying information indicating that the scheduled change value of the set value is abnormal to the display (130) of the portable terminal constituting the quality determination apparatus (13).

In the processing of Step ST112, the subject to which the arithmetic unit (60) transmits the "instruction for displaying information indicating that the scheduled change value of the set value is abnormal" may be, for example, a personal computer or a management server used by an operation manager of a container ship.

(Step ST113)

In the processing of Step ST113, to continue the adjustment of the blowout temperature set value, the oxygen concentration set value, and the carbon dioxide concentration set value, the arithmetic unit (60) of the quality determination apparatus (13) returns to Step ST106 and performs the processing after Step ST106 again. To end the adjustment of the blowout temperature set value, the oxygen concentration set value, and the carbon dioxide concentration set value, the arithmetic unit (60) of the quality determination apparatus (13) ends the processing for adjusting these set values.

—Features of Fourth Embodiment—

In the quality determination apparatus (13) of the present embodiment, the learning unit (104) generates the state estimation models (111 to 113), and the inference unit (106) calculates an estimated value of the state index (chlorophyll fluorescence intensity in the present embodiment) using the state estimation models (111 to 113). Thus, according to the present embodiment, the estimated value of the state index can be calculated using so-called machine learning, and whether the sign condition is met can be accurately determined using the calculated estimated value of the state index.

In the quality determination apparatus (13) of the present embodiment, the inference unit (106) uses the state estimation model (111 to 113) generated by machine learning to calculate the scheduled change values of the suction temperature set value, the oxygen concentration set value, and the carbon dioxide concentration set value. Thus, according to the present embodiment, each of the suction temperature set value, the oxygen concentration set value, and the carbon dioxide concentration set value can be set to an appropriate value, keeping the target articles (7) from degradation.

—First Variation of Fourth Embodiment—

For the environmental information acquired by the information acquisition unit (102) of the present embodiment, the measurements included in the environmental information described above are merely examples. The environmental information acquired by the information acquisition unit (102) may include, for example, a measurement of the evaporation pressure of the refrigerant in the refrigerant circuit (21), a measurement of the relative humidity of the air in the cargo space (5), and a measurement of the ethylene concentration of the air in the cargo space (5). The evaporation pressure of the refrigerant in the refrigerant circuit (21) is a physical quantity indicating the operating state of the container refrigeration apparatus (20) and correlating with the temperature of the cargo space (5). The environment information acquired by the information acquisition unit (102) may exclude some of the above-described measurements.

When the shipping container (1) is equipped with the container refrigeration apparatus (20) only out of the container refrigeration apparatus (20) and the air composition adjustment apparatus (40), the measurements of the oxygen concentration and the carbon dioxide concentration are excluded from the environmental information. In this case, the environmental information desirably includes a "ventilation amount of the cargo space (5)."

—Second Variation of Fourth Embodiment—

The computer in which the quality determination program of the present embodiment is installed is not limited to the portable terminal. In the context of this specification, the "computer" refers to a "machine that stores a program describing a procedure (algorithm) of calculation and automatically executes the calculation according to the stored program." Thus, the computer in which the quality determination program of the present embodiment is installed may be, for example, a tablet, laptop, or desktop personal computer, or a microcomputer incorporated in a controller of the container refrigeration apparatus (20).

Other Embodiments

The quality determination apparatus (13) of each of the first to fourth embodiments may be modified in the following manner. The following variations may be combined or replaced as needed, as long as the functions of the quality determination apparatus (13) are not impaired.

—First Variation—

The quality determination unit (64) of each of the first to third embodiments may be configured not to execute the notification operation or the diagnosis instruction operation in the main operation. The quality determination unit (64) of each of the first to third embodiments may be configured not to execute the cause identification operation and the environment change operation in the main operation.

—Second Variation—In the quality determination apparatus (13) of each of the first to fourth embodiments, the state index sensor (15) may be a sensor that detects whether the target articles (7) have ice. In this case, the state index sensor (15) detects whether the target articles (7) have ice as the state index. A spectrometer capable of measuring absorption spectra of water (liquid) and ice can be used as the state index sensor (15) of this variation.

The quality determination apparatus (13) of the present variation sets a "condition that the state index sensor (15) has detected the presence of ice" as the sign condition. When this sign condition is met, the quality determination apparatus (13) of the present variation determines that the target articles (7) show the sign of degradation.

If moisture contained in the target articles (7) freezes, the target articles are degraded. Such degradation due to freezing occurs not only when the target articles (7) are the fruits and vegetables, but also when the target articles (7) are, for example, liquid pharmaceutical products. Thus, the target articles (7) whose sign of degradation is determined by the quality determination apparatus (13) of the present variation are not limited to the fresh produce, and may be, for example, pharmaceutical products.

—Third Variation—

In each of the first to fourth embodiments, the state index sensor (15) of the quality determination apparatus (13) may be configured to measure, as the state index, a leakage amount of internal components of cells from the fresh produce which is the target articles (7). Damage to the cell membrane of the fresh produce causes the internal components of the cells of the fresh produce to leak, resulting in a decrease in the electrical resistance of the fresh produce. Thus, the state index sensor (15) of the present variation can be a sensor that measures the electrical resistance of the fresh produce which is the target articles (7) and estimates the leakage amount of the internal components of the cells of the fresh produce based on the measured electrical resistance. The quality determination apparatus (13) of the present variation defines a condition that "the leakage amount of the internal components of the cells of the fresh produce" exceeds a predetermined reference value as the sign condition.

—Fourth Variation—

In each of the first to fourth embodiments, the state index sensor (15) of the quality determination apparatus (13) may be configured to measure, as the state index, the concentration of a stress-related plant hormone generated from the fresh produce which is the target articles (7). Examples of the plant hormone of this kind include ethylene, abscisic acid, brassinosteroids, and jasmonic acid. A gas sensor that measures the concentrations of such substances can be used as the state index sensor (15) of this variation. The quality determination apparatus (13) of the present variation defines a condition that the concentration of the substance measured by the state index sensor (15) has exceeded a predetermined reference value as the sign condition.

—Fifth Variation—

In each of the first to fourth embodiments, the state index sensor (15) of the quality determination apparatus (13) may be configured to measure, as the state index, the concentration of a substance generated by anaerobic respiration of the fresh produce which is the target articles (7). Examples of such a substance include acetaldehyde and ethanol. A gas sensor that measures the concentrations of such substances can be used as the state index sensor (15) of this variation. The quality determination apparatus (13) of the present variation defines a condition that the concentration of the substance measured by the state index sensor (15) has exceeded a predetermined reference value as the sign condition.

In addition, when the fresh produce takes anaerobic respiration, the fresh produce releases carbon dioxide without consuming oxygen. Thus, the state index sensor (15) of the present variation can be a sensor that calculates the respiratory quotient (the amount of carbon dioxide released/the amount of oxygen consumed) of the fresh produce which is the target articles (7). In this case, the quality determination apparatus (13) defines a condition that the respiratory quotient has exceeded a predetermined reference value as the sign condition.

—Sixth Variation—

In each of the first to fourth embodiments, the state index sensor (15) of the quality determination apparatus (13) may be configured to measure, as the state index, the degree of internal browning of the fresh produce which is the target articles (7). A sensor that irradiates the fresh produce with light to measure the degree of internal browning without breaking the fresh produce can be used as the state index sensor (15) of this variation. The quality determination apparatus (13) of the present variation defines a condition that the degree of internal browning measured by the state index sensor (15) has exceeded a predetermined reference value as the sign condition.

—Seventh Variation—

In each of the first to fourth embodiments, the state index sensor (15) of the quality determination apparatus (13) may be configured to measure, as the state index, the concentration of phenol, chlorogenic acid, or carotene contained in the fresh produce which is the target articles (7). The quality determination apparatus (13) of the present variation defines a condition that the concentration of the substance measured by the state index sensor (15) has exceeded a predetermined reference value as the sign condition.

—Eighth Variation—

In each of the first to fourth embodiments, the state index sensor (15) of the quality determination apparatus (13) may be configured to measure, as the state index, pH of the fresh produce which is the target articles (7). The quality determination apparatus (13) of the present variation defines a condition that the pH measured by the state index sensor (15) has exceeded a predetermined reference value as the sign condition.

—Ninth Variation—

The shipping container (1) equipped with the internal environment control system (10) including the quality determination apparatus (13) of any of the first to fourth embodiments and the variations is not limited to a shipping container for marine transportation, and may be a shipping container for land transportation. The target to be equipped with the internal environment control system (10) is not limited to the shipping container (1). That is, the internal environment control system (10) may be installed in, for example, a cold storage warehouse, and a commercial refrigerator.

While the embodiment and variations thereof have been described above, it will be understood that various changes in form and details may be made without departing from the spirit and scope of the claims. The foregoing embodiments and variations thereof may be combined and replaced with each other without deteriorating the intended functions of the present disclosure.

INDUSTRIAL APPLICABILITY

As can be seen in the foregoing, the present disclosure is useful for a quality determination apparatus.

EXPLANATION OF REFERENCES

5 Cargo Space (Storage Space)
7 Target Article
13 Quality Determination Apparatus
14 Environment Adjustment Apparatus
15 State Index Sensor (State Detector)
64 Quality Determination Unit (Main Processing Unit)
75 Communication Unit (State Acquisition Unit)
80 Operation Panel (Notification Device)
101 State Acquisition Unit
102 Information Acquisition Unit
103 Setting Acquisition Unit
104 Learning Unit
111 First State Estimation Model
112 Second State Estimation Model
113 Third State Estimation Model
130 Display of Portable Terminal (Notification Device)

The invention claimed is:

1. A quality determination apparatus, comprising:
a state acquisition unit configured to acquire a state index indicating a state of a target article contained in a storage space where an internal environment is controlled from a state detector that detects the state index; and
a main processing unit configured to perform a determination operation of determining whether a sign condition indicating a sign of degradation of the target article is met based on the state index acquired by the state acquisition unit,
the state acquisition unit being configured to acquire, as the state index, an intensity of chlorophyll fluorescence of fresh produce which is the target article,
the sign condition being a condition that the intensity of chlorophyll fluorescence acquired by the state acquisition unit exceeds a reference fluorescence intensity,
the main processing unit being configured to perform a reference setting operation of setting the reference fluorescence intensity, and
the main processing unit being configured to set the reference fluorescence intensity, based on the intensity of chlorophyll fluorescence acquired by the state acquisition unit when an oxygen concentration in the storage space is lowered in the reference setting operation as compared to before the reference setting operation.

2. The quality determination apparatus of claim 1, wherein
when determining that the sign condition is met, the main processing unit is configured to perform an environment change operation of instructing an environment adjustment apparatus that adjusts the internal environment of the storage space to change the internal environment of the storage space in order to keep the target article from degradation.

3. A quality determination apparatus, comprising:
a state acquisition unit configured to acquire a state index indicating a state of a target article contained in a storage space where an internal environment is controlled from a state detector that detects the state index; and
a main processing unit configured to perform a determination operation of determining whether a sign condition indicating a sign of degradation of the target article is met based on the state index acquired by the state acquisition unit,
the state acquisition unit being configured to acquire, as a state index, an intensity of chlorophyll fluorescence of fresh produce which is the target article,
the sign condition being a condition that the intensity of chlorophyll fluorescence acquired by the state acquisition unit exceeds a reference fluorescence intensity,
when determining that the sign condition is met, the main processing unit being configured to perform a cause identification operation of identifying, from a plurality of environmental indexes indicating the internal environment of the storage space, an environmental index that causes the sign of degradation of the target article, and
in the cause identification operation, the main processing unit identifying, from the plurality of environmental indexes, the environmental index that causes the sign of degradation of the target article by using respective average values for the plurality environmental indexes over a past predetermined period and respective current values of the plurality of environmental indexes.

4. The quality determination apparatus of claim 1, wherein
when determining that the sign condition is met, the main processing unit is configured to perform a notification operation of instructing a notification device that notifies a human of information to notify a possibility of degradation of the target article.

5. The quality determination apparatus of claim 1, wherein
when determining that the sign condition is met, the main processing unit is configured to perform a diagnosis instruction operation of instructing an environment adjustment apparatus that adjusts the internal environment of the storage space to diagnose whether a component of the environment adjustment apparatus functions normally.

6. The quality determination apparatus of claim 1, further comprising:
an information acquisition unit configured to acquire environmental information about the internal environment of the storage space;
a setting acquisition unit configured to acquire setting information that is a set value of an environmental index indicating the internal environment of the storage space; and
a learning unit configured to generate a state estimation model that has learned a correlation between the state index detected by the state detector, the environmental information acquired by the information acquisition unit, and the setting information acquired by the setting acquisition unit, wherein
the main processing unit is configured to determine whether the sign condition is met based on an estimated value of the state index calculated by inputting the environmental information and the setting information to the state estimation model.

7. The quality determination apparatus of claim 6, wherein
when determining that the sign condition is met, the main processing unit is configured to perform an environment change operation of instructing an environment adjustment apparatus that adjusts the internal environment of the storage space to change the internal environment of the storage space in order to keep the target article from degradation, and
in the environment change operation, the main processing unit is configured to instruct the environment adjustment apparatus to change the set value of the environmental index based on a result of comparison between the estimated value of the state index calculated by inputting the environment information and the setting information to the state estimation model and a predetermined reference value.

8. The quality determination apparatus of claim 6, wherein
the environmental information acquired by the information acquisition unit includes at least one of temperature, oxygen concentration, or carbon dioxide concentration of air in the storage space.

9. The quality determination apparatus of claim 6, wherein
the environmental information acquired by the information acquisition unit includes a physical quantity indicating an operating state of a refrigeration apparatus that adjusts a temperature of the storage space and correlating with the temperature of the storage space.

10. The quality determination apparatus of claim 7, wherein
when the set value of the environmental index changed in the environment change operation is an abnormal value deviated from a predetermined reference range, the main processing unit is configured to instruct a notification device that notifies a human of information to notify that the changed set value of the environmental index is abnormal.

* * * * *